United States Patent [19]

Holdgrün et al.

[11] Patent Number: 5,756,422
[45] Date of Patent: May 26, 1998

[54] SUBSTITUTED QUINOLINE COMPOUNDS AND THEIR USE AS SAFENERS

[75] Inventors: Xenia Holdgrün, Kelkheim; Lothar Willms, Hofheim; Klaus Bauer, Hanau; Hermann Bieringer, Eppstein, all of Germany

[73] Assignee: Hoechst Schering AgrEvo GmbH, Berlin, Germany

[21] Appl. No.: 535,028

[22] PCT Filed: May 2, 1994

[86] PCT No.: PCT/EP94/01396

§ 371 Date: Oct. 18, 1995

§ 102(e) Date: Oct. 18, 1995

[87] PCT Pub. No.: WO94/26716

PCT Pub. Date: Nov. 24, 1994

[30] Foreign Application Priority Data

May 7, 1993 [DE] Germany ............... 43 15 153.1

[51] Int. Cl.⁶ ............ A01N 43/42; C07D 215/28
[52] U.S. Cl. ............ 504/105; 504/108; 544/128; 546/14; 546/23; 546/153; 546/159; 546/171; 546/172; 546/174; 546/175; 546/177; 546/178
[58] Field of Search ............ 504/108, 105; 544/128; 546/14, 23, 153, 159, 171, 172, 174, 175, 177, 178

[56] References Cited

U.S. PATENT DOCUMENTS

| | | | |
|---|---|---|---|
| 4,902,340 | 2/1990 | Hubele | 504/105 |
| 5,023,333 | 6/1991 | Hubele | 546/175 |
| 5,102,445 | 4/1992 | Hubele | 504/105 |

FOREIGN PATENT DOCUMENTS

| | | |
|---|---|---|
| 0 094 349 | 11/1983 | European Pat. Off. . |
| 0 258 184 | 3/1988 | European Pat. Off. . |
| 0 492 366 | 7/1992 | European Pat. Off. . |

*Primary Examiner*—Richard L. Raymond
*Attorney, Agent, or Firm*—Frommer Lawrence & Haug LLP

[57] ABSTRACT

Substituted quinoline compounds, processes for their preparation, composition containing them, and their use as safeners Compounds of the formula I and salts thereof

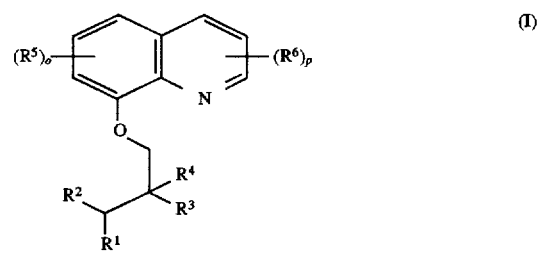

in which $R^1$ [lacuna] CN, C(=Z)—Q(A$_j$X$_i$)$_q$—R, —C(=Z)—QR*, 1,2,3,4-tetrazol-5-yl, 1,3,4-triazol-2-yl, 1,3-oxazol-2-yl, and the remaining radicals are as defined in claim 1, are suitable for use as safeners for protecting crop plants such as, for example, cereals, rice and maize, against herbicide damage.

Some of the compounds are known and some are novel and they can be prepared from quinolin-8-oxy derivatives by the processes of claim 7.

12 Claims, No Drawings

SUBSTITUTED QUINOLINE COMPOUNDS AND THEIR USE AS SAFENERS

This application is a Rule 371 of PCT/EP94/01396, filed May 2, 1994.

The invention relates to the technical field of the crop protection products, in particular combinations of active substance and antidote, which are outstandingly suitable for the use against competing harmful plants in crops of useful plants.

When plant treatment products, in particular herbicides are used, it is possible that the treated crop plants show undesired damage. Many herbicides are not fully tolerated (selective) by some important crop plants, such as maize, cereals or rice, so that their use is restricted within narrow limits. This is why they can sometimes not be employed at all, or only at such low application rates that the desired broad herbicidal activity against the harmful plants is not guaranteed. For example, many herbicides of the substance classes mentioned further below cannot be employed selectively in maize, cereals or rice. In particular when herbicides are applied post-emergence, the crop plants show phytotoxic secondary effects, and it is desirable to avoid, or reduce, such a phytotoxicity.

It is already known to employ herbicides in combination with compounds which reduce the phytotoxicity of the herbicides in crop plants without analogously reducing the herbicidal activity against the harmful plants. Such components in combinations are termed safeners or antidotes.

EP-A-86750 describes quinolin-8-oxymethane- and -ethanecarbonitriles and -amide oximes as safeners for phenoxyphenoxyalkanecarboxylic esters and sulfonylureas. EP-A-94349 (U.S. Pat. No. 4,902,340) discloses the use of suitable carboxylic esters and EP-A-138773 (U.S. Pat. No. 4,749,406) discloses the use of 8-alkyloxy- and 8-alkenyloxyquinolines as safeners for herbicides of a range of structural classes. EP-A-254222 mentions quinolin-8-oxyacetaldehyde acetals as safeners for a range of classes of herbicides. EP-A-159287 describes the use of quinolin-8-oxyacetic acid and -propionic acid derivatives as safeners specifically for imidazolinone herbicides. EP-A-159290 (AU-A-4041285), EP-A-191736 (U.S. Pat. No. 4,881,966) and EP-A-258184 (AU-A-7681587) disclose the use of the same quinoline compounds as safeners for aryloxyphenoxyalkanecarboxylic ester herbicides. EP-A-407341 describes the use of these compounds as safeners for herbicidal N-benzoyl-N-phenylalanines. EP-A-492366 mentions quinolin-8-oxyacetic acid derivatives as safeners for herbicides of a range of structural classes.

It has now been found that, surprisingly, a group of quinoline derivatives of the formula I below is outstandingly suitable for protecting crop plants against harmful effects of aggressive agrochemicals, in particular herbicides.

Compounds according to the invention which are suitable for protecting crop plants against damaging effects of aggressive agrochemicals are compounds of the formula I or salts thereof

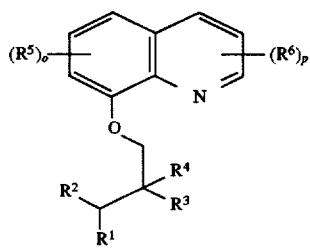

(I)

in which $R^1$ is a radical of the formula

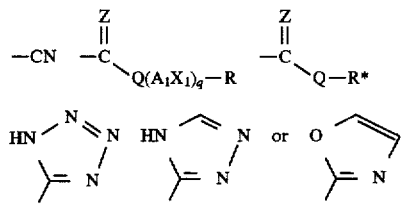

in which $R^*$, R, Z, Q, $A_i$, $X_i$ and q are as defined further below, $R^2$ is hydrogen, $C_1$–$C_8$-alkyl, $C_1$–$C_8$-haloalkyl, $C_2$–$C_8$-alkenyl, $C_2$–$C_8$-alkynyl, $C_3$–$C_7$-cycloalkyl, benzyl, where each of the last-mentioned six radicals is unsubstituted or substituted by one or more radicals selected from the group comprising halogen, cyano, nitro, hydroxyl, thio, $C_1$–$C_4$-alkyl, $C_1$–$C_4$-haloalkyl, the latter two substituents only in the case of cyclic radicals, or $C_1$–$C_4$-alkoxy and $C_1$–$C_4$-haloalkoxy, or is $SiR^a{}_3$, in which the $R^a$ radicals independently of one another are $C_1$–$C_4$-alkyl, $C_2$–$C_4$-alkenyl, $C_2$–$C_4$-alkynyl, benzyl, phenyl or substituted phenyl, $R^3$ is $OR^7$, $SR^7$, $NR^8{}_2$, $P(Y)R^9{}_2$, $S(O)_n$—$R^{10}$ or $OR^{10}$, in which n is 0, 1 or 2 and Y is O or S and $R^7$, $R^8$, $R^9$ and $R^{10}$ are as defined further below, $R^4$ is hydrogen, $C_1$–$C_8$-alkyl, $C_1$–$C_8$-haloalkyl, $C_2$–$C_8$-alkenyl, $C_2$–$C_8$-alkynyl, $C_3$–$C_7$-cycloalkyl, benzyl, where each of the last-mentioned six radicals is unsubstituted or substituted by one or more radicals selected from the group comprising halogen, cyano, nitro, hydroxyl, thio, $C_1$–$C_4$-alkyl, $C_1$–$C_4$-haloalkyl, the latter two substituents only in the case of cyclic radicals, or $C_1$–$C_4$-alkoxy and $C_1$–$C_4$-haloalkoxy, or is $OR^{11}$ or $S(O)_n$—$R^{11}$, or $R^3$ and $R^4$ together are =O, =S or a diradical of the formula —$Q^1$—A—$Q^2$—, in which $Q^1$ and $Q^2$ are defined analogously to Q and A is unsubstituted or substituted $C_2$–$C_4$-alkylene or $C_2$–$C_4$-alkenylene, and $R^5$ and $R^6$ are identical or different radicals which, independently of one another, are hydrogen, halogen, nitro, cyano, amino or $C_1$–$C_8$-alkyl, $C_1$–$C_4$-acyl, $C_1$–$C_8$-alkoxy, mono($C_1$–$C_4$-alkyl)amino, di($C_1$–$C_4$-alkyl)amino, $C_1$–$C_8$-alkylthio, $C_1$–$C_8$-alkylsulfinyl or $C_1$–$C_8$-alkylsulfonyl, where each of the last-mentioned eight radicals is unsubstituted or substituted by one or more, preferably up to 3, identical or three different substitutents selected from the group comprising halogen, nitro, cyano, hydroxyl, thio, $C_1$–$C_8$-haloalkoxy, $C_1$–$C_8$-alkoxy, $C_1$–$C_8$-(alkoxypolyalkyleneoxy) having preferably up to four oxygen atoms, $C_1$–$C_8$-alklythio, $C_1$–$C_6$-alkylsulfinyl, $C_1$–$C_6$-alkylsulfonyl, $C_2$–$C_8$-alkenyloxy, $C_2$–$C_8$-alkynyloxy, $C_2$–$C_8$-alkenylthio, $C_2$–$C_8$-alkynylthio, $C_3$–$C_7$-cycloalkyl, $C_3$–$C_7$-cycloalkoxy, mono and di($C_1$–$C_4$-alkyl)amino and $C_1$–$C_8$-alkoxycarbonyl, and are preferably hydrogen, halogen, $C_1$–$C_6$-haloalkyl, such as trifluoromethyl, $C_1$–$C_6$-haloalkoxy, such as difluoromethoxy, $C_1$–$C_6$-alkyl, $C_1$–$C_6$-alkoxy, $C_1$–$C_6$-alkylthio, $C_1$–$C_6$-alkylsulfonyl, nitro, amino, mono ($C_1$–$C_4$-alkyl)amino, di($C_1$–$C_4$-alkyl)amino, nitro or cyano, o is an integer from 1 to 3, p is an integer from 1 to 3, R is hydrogen or an aliphatic, aromatic, heteroaromatic, araliphatic or heteroaliphatic radical having 1 to 30 carbon atoms and, if appropriate, one or more functional groups, for example hydrogen, $C_1$–$C_{18}$-alkyl, $C_3$–$C_{12}$-cycloalkyl, $C_2$–$C_8$-alkenyl, $C_2$–$C_8$-alkynyl, heterocyclyl, phenyl or heteroaryl, where each of the above radicals independently of one another is unsubstituted or substituted by one or more radicals selected from the group comprising halogen, cyano, nitro, thio, hydroxyl, $C_1$–$C_8$-alkyl, $C_1$–$C_8$-haloalkyl, the latter two substituents only in the case of cyclic radicals, or $C_1$–$C_8$-alkoxy, $C_2$–$C_8$-alkenyloxy, $C_2$–$C_8$-alkynyloxy, $C_1$–$C_8$-haloalkoxy, $C_1$–$C_8$-alkylthio, $C_2$–$C_8$-alkenylthio, $C_2$–$C_8$-alkynylthio, $C_3$–$C_7$-cycloalkyl, $C_3$–$C_7$-cycloalkoxy, radicals of the formulae —$NR^bR^c$, —CO—$NR^bR^c$ and —O—CO—$NR^bR^c$, where $R^b$ and $R^c$ in the last-mentioned three radicals independently of one another are hydrogen, $C_1$–$C_8$-alkyl, $C_2$–$C_8$-alkenyl, $C_2$–$C_8$-alkynyl, benzyl, phenyl, substituted phenyl or, together with the nitrogen atom, are a 3- to 8-membered heterocycle which can also contain up to two further heteroatoms selected from the group comprising N, O and S and which can be substituted by $C_1$–$C_4$-alkyl, and also ($C_1$–$C_8$-alkoxy)carbonyl, ($C_1$–$C_8$-alkoxy)thiocarbonyl, ($C_2$–$C_8$-alkenyloxy)carbonyl, ($C_2$–$C_8$-alkynyloxy)carbonyl, ($C_1$–$C_8$-alkylthio)carbonyl, ($C_2$–$C_8$-alkenylthio)carbonyl, ($C_2$–$C_8$-alkynylthio)carbonyl, formyl, ($C_1$–$C_8$-alkyl)carbonyl, ($C_2$–$C_8$-alkenyl)carbonyl, ($C_2$–$C_8$-alkynyl)carbonyl, $C_1$–$C_4$-alkylimino, $C_1$–$C_4$-alkoximino, ($C_1$–$C_8$-alkyl)carbonylamino, ($C_2$–$C_8$-alkenyl)carbonylamino, ($C_2$–$C_8$-alkynyl)carbonylamino, ($C_1$–$C_8$-alkoxy)carbonylamino, ($C_2$–$C_8$-alkenyloxy)carbonylamino, ($C_2$–$C_8$-alkynyloxy)carbonylamino, ($C_1$–$C_8$-alkylamino)carbonylamino, ($C_1$–$C_8$-alkyl)carbonyloxy, which is unsubstituted or substituted by halogen, nitro, $C_1$–$C_4$-alkoxy or optionally substituted phenyl, and also ($C_2$–$C_6$-alkenyl)carbonyloxy, ($C_2$–$C_6$-alkynyl)carbonyloxy, ($C_1$–$C_8$-alkyloxy)carbonyloxy, ($C_2$–$C_6$-alkenyloxy)carbonyloxy, ($C_2$–$C_6$-alkynyloxy)carbonyloxy, $C_1$–$C_8$-alkylsulfonyl, $C_1$–$C_8$-alkylsulfinyl, phenyl, phenyl-$C_1$–$C_6$-alkoxy, phenyl ($C_1$–$C_6$-alkoxy)carbonyl, phenoxy, phenoxy-$C_1$–$C_6$-alkoxy, phenoxy($C_1$–$C_6$-alkoxy)carbonyl, phenoxycarbonyl, phenylcarbonyloxy, phenylcarbonylamino, phenyl($C_1$–$C_6$-alkyl)carbonylamino and phenyl($C_1$–$C_6$-alkyl)carbonyloxy, the last-mentioned eleven radicals being unsubstituted in the phenyl ring or substituted by one or more radicals selected from the group comprising halogen, cyano, $C_1$–$C_4$-alkyl, $C_1$–$C_4$-alkoxy, $C_1$–$C_4$-haloalkyl, $C_1$–$C_4$-haloalkoxy and nitro, and also radicals of the formulae —$SiR^d_3$, —O—$Si(R^d)_3$ and $(R^d)_3Si$—$C_1$–$C_6$-alkoxy, where the $R^d$ radicals in the abovementioned formulae, independently of one another, are $C_1$–$C_4$-alkyl, $C_2$–$C_4$-alkenyl, benzyl, phenyl or substituted phenyl, and —CO—$ONR^e_2$, —O—N=$CR^e_2$, —N=$CR^e_2$, —O—$NR^e_2$, —$CH(OR^e)_2$ and —O—$(CH_2)_m$—CH $(OR^e)_2$, where the $R^e$ radicals in the abovementioned formulae, independently of one another, are hydrogen, $C_1$–$C_4$-alkyl or phenyl which is unsubstituted or mono- or polysubstituted by radicals selected from the group comprising halogen, cyano, $C_1$–$C_4$-alkyl, $C_1$–$C_4$-alkoxy, $C_1$–$C_4$-haloalkyl, $C_1$–$C_4$-haloalkoxy and nitro, or, in pairs, are a $C_2$–$C_6$-alkylene chain and m is 0 to 6, and a substituted radical of the formula $R^fO$—

$CHR^g$—$CH(OR^f)$—, in which the $R^f$ radicals, independently of one another, are $C_1$–$C_4$-alkyl or together are a $C_1$–$C_6$-alkylene group and $R^g$ is hydrogen or $C_1$–$C_4$-alkyl, and a radical of the formula I'

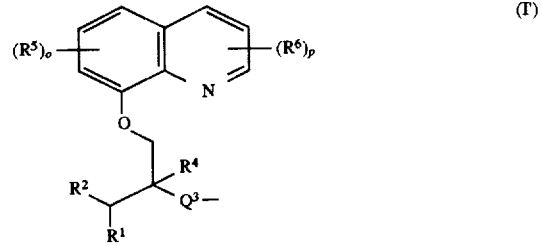

in which $R^1$, $R^2$, $R^4$, $R^5$, $R^6$, o and p are defined analogously to the same symbols in formula I and $Q^3$ is defined analogously to Q, R* is a radical of the formula —CO—R, —CS—R, —$NR^hR^i$, —N=$CR^jR^k$ or $SiR^m_3$, in which R has the abovementioned meaning and $R^h$, $R^i$, $R^j$ and $R^k$ independently of one another are hydrogen, $C_1$–$C_4$-alkyl, $C_2$–$C_4$-alkenyl, $C_2$–$C_4$-alkynyl, benzyl, phenyl or substituted phenyl, or $R^h$ and $R^i$ together with the nitrogen atom are a 5- or 6-membered heterocycle which can also contain up to two further heteroatoms selected from the group comprising N, O and S and which can be substituted by $C_1$–$C_4$-alkyl, or $R^j$ and $R^k$ together are a $C_2$–$C_6$-alkylene group and the radicals $R^m$, independently of one another, are $C_1$–$C_4$-alkyl, $C_2$–$C_4$-alkenyl, $C_2$–$C_4$-alkynyl, benzyl, phenyl or substituted phenyl, $R^7$ is a radical analogous to R*, $R^8$ radicals independently of one another are hydrogen, unsubstituted or substituted $C_1$–$C_4$-alkyl, $C_1$–$C_4$-haloalkyl, $C_2$–$C_4$-alkenyl, $C_2$–$C_4$-alkynyl, $C_3$–$C_6$-cycloalkyl, $C_3$–$C_6$-cycloalkenyl, heterocyclyl, aryl or heteroaryl, $R^9$ radicals independently of one another are hydrogen, unsubstituted or substituted $C_1$–$C_8$-alkyl, $C_1$–$C_8$-haloalkyl, $C_2$–$C_8$-alkenyl, $C_2$–$C_8$-alkynyl, $C_3$–$C_7$-cycloalkyl, $C_1$–$C_8$-alkoxy, $C_2$–$C_8$-alkenyloxy, $C_2$–$C_8$-alkynyloxy, $C_1$–$C_8$-haloalkoxy, $C_3$–$C_7$-cycloalkoxy, phenyl, phenoxy, the last-mentioned two radicals in the phenyl ring being unsubstituted or substituted by one or more radicals selected from the group comprising halogen, cyano, $C_1$–$C_4$-alkyl, $C_1$–$C_4$-alkoxy, $C_1$–$C_4$-haloalkyl, $C_1$–$C_4$-haloalkoxy and nitro, $R^{10}$ is a radical which is analogous to R, $R^{11}$ is a radical which is analogous to R, Z is O, S, $NR^8$, $NOR^8$ or N—O—CO—$R^{12}$, $R^{12}$ is unsubstituted or substituted $C_1$–$C_4$-alkyl, $C_1$–$C_4$-haloalkyl, $C_2$–$C_4$-alkenyl, $C_2$–$C_4$-alkynyl, $C_3$–$C_6$-cycloalkyl, $C_3$–$C_6$-cycloalkenyl, heterocyclyl, aryl or heteroaryl, Q is O, S, $NR^8$ or $NR^8$—$NR^8$, $X_i$ radicals independently of one another are O, S, $NR^8$ or N—$(A_iX_i)_q$—R, $A_i$ radicals independently of one another are unsubstituted or substituted $C_1$–$C_6$-alkylene, $C_2$–$C_6$-alkenylene, $C_2$–$C_6$-alkynylene, $C_3$–$C_6$-cycloalkylene, $C_3$–$C_6$-cycloalkenylene, heterocyclylene, arylene or heteroarylene, i is a consecutive number which, if q is unequal to 0, assumes the meaning of all integers from 1 to q, where q has the meaning given below, q indices independently of one another are integers from 0 to 4, the total of the numbers q being limited, preferably to up to 6, in particular up to 4.

In the formula (I) and hereinafter, the radicals alkyl, alkoxy, haloalkyl, haloalkoxy, alkylamino, alkylthio, alkylsulfinyl and alkylsulfonyl and the corresponding unsaturated and/or substituted radicals in the carbon skeleton can in each case be straight-chain or branched. Unless specifically mentioned, preferred carbon skeletons in these radicals are those having 1 to 4 carbon atoms and, in the case of unsaturated groups, 2 to 4 carbon atoms. Alkyl radicals, also in the composite meanings, such as alkoxy, haloalkyl and the like are, for example, methyl, ethyl, n- or i-propyl, n-, i-, t- or 2-butyl, pentyls, hexyls, such as n-hexyl, i-hexyl and 1,3-dimethylbutyl, heptyl, such as n-heptyl, 1-methylhexyl and 1,4-dimethylpentyl; alkenyl and alkynyl radicals have the meanings of the unsaturated radicals which correspond to the alkyl radicals, for example alkenyl is allyl, 1-methylprop-2-en-1-yl, 2-methylprop-2-en-1-yl., but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl. Halogen is fluorine, chlorine, bromine or iodine, preferably fluorine, chlorine or bromine, in particular fluorine or chlorine. Haloalkyl, haloalkenyl and haloalkynyl are alkyl, alkenyl or alkynyl, each of which is partially or completely substituted by halogen, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $OCF_2CF_3$, $OCH_2CF_3$. The same applies analogously to haloalkenyl and other halogen-substituted radicals.

Aryl is, for example, phenyl, naphthyl, tetrahydronaphthyl, indenyl, indanyl, pentalenyl, fluorenyl, and the like, preferably phenyl; aryloxy is preferably the oxy radicals which correspond to the abovementioned aryl radicals, in particular phenoxy.

Heteroaryl, or heteroaryl in heteroaryloxy, is, for example, pyridyl, pyrimidinyl, pyridazinyl, pyrazinyl, thienyl, thiazolyl, oxazolyl, furyl, pyrrolyl, pyrazolyl and imidazolyl, but also bicyclic or polycyclic aromatic or araliphatic compounds, for example quinolinyl, benzoxazolyl and the like.

Substituted aryl or aryloxy, heteroaryl, heteroaryloxy, phenyl, phenoxy, benzyl, benzyloxy, or substituted bycyclic radicals which have aromatic moieties are, for example, a substituted radical which is derived from the unsubstituted basic structure, the substituents being, for example, one or more, preferably 1, 2 or 3 radicals selected from the group comprising halogen, alkyl, haloalkyl, alkoxy, haloalkoxy, hydroxyl, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl, and, in the case of radicals which have carbon atoms, those having 1 to 4 carbon atoms, in particular 1 or 2, are preferred. Preferred are, as a rule, substituents selected from the group comprising halogen, for example fluorine and chlorine, $C_1$–$C_4$-alkyl, preferably methyl or ethyl, $C_1$–$C_4$-haloalkyl, preferably trifluoromethyl, $C_3$–$C_4$-alkoxy, preferably methoxy or ethoxy, $C_1$–$C_4$-haloalkoxy, nitro and cyano. Particularly preferred are the substituents methyl, methoxy and chlorine.

Optionally substituted phenyl is, for example, phenyl which is unsubstituted or mono- or polysubstituted, preferably up to trisubstituted, by identical or different radicals selected from the group comprising halogen, $C_1$–$C_4$-alkyl, $C_1$–$C_4$-alkoxy, $C_1$–$C_4$-haloalkyl, $C_1$–$C_4$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, and o-, m- and p-methoxyphenyl.

A three- to seven-membered heterocyclic radical as described above is preferably derived from benzene, of which at least one CH is replaced by N and/or at least two adjacent CH pairs are replaced by NH, S and/or O. The radical may be benzo-fused. It is optionally partially or completely hydrogenated, in which case it is also termed heterocyclyl. Suitable radicals are, in particular, oxiranyl, pyrrolidyl, piperidyl, dioxolanyl, pyrazolyl, morpholyl, furyl, tetrahydrofuryl, indolyl, quinolinyl, pyrimidyl, azepinyl, triazolyl, thienyl and oxazolyl.

Acyl is, for example, formyl, alkylcarbonyl, such as ($C_1$–$C_4$-alkyl)carbonyl, phenylcarbonyl, it being possible for the phenyl ring to be substituted, for example as shown above for phenyl, or alkoxycarbonyl, phenyloxycarbonyl, benzyloxycarbonyl, alkylsulfonyl and other organic acid radicals.

Some compounds of the formula I contain one or more asymmetric carbon atoms or double bonds which are not specifically indicated in the formula I. The stereoisomers which are possible and which are defined by their specific spatial arrangement, such as enantiomers, diastereomers, E and Z isomers and their mixtures are, however, all embraced by the formula I.

The compounds of the formula I which are derived from carboxylic acids can form salts, in which the radical R is replaced by an equivalent of an agriculturally suitable cation. Examples of these salts are metal salts, in particular alkali metal salts or alkaline earth metal salts, but also ammonium salts or salts with organic amines, and salts which contain sulfonium or phosphonium ions as cations.

Particularly suitable as salt formers are metals and organic nitrogen bases, especially quaternary ammonium bases. Metals which are suitable for salt formation are alkaline earth metals, such as magnesium or calcium, but especially alkali metals, such as lithium and, in particular, potassium and sodium.

Nitrogen bases which are suitable for salt formation are primary, secondary or tertiary, aliphatic and aromatic amines which are optionally hydroxylated on the hydrocarbon radical, such as methylamine, ethylamine, propylamine, isopropylamine, the four butylamine isomers, dimethylamine, diethyamine, dipropylamine, diisopropylamine, di-n-butylamine, pyrrolidine, piperidine, morpholine, trimethylamine, triethylamine, tripropylamine, quinuclidine, pyridine, quinoline, isoquinoline and methanolamine, ethanolamine, propanolamine, dimethanolamine, diethanolamine or triethanolamine.

Examples of quaternary ammonium bases are tetraalkylammonium cations in which the alkyl radicals independently of one another are straight-chain or branched $C_1$–$C_8$-alkyl groups, such as the tetramethylammonium cation, the tetraethylammonium cation or the trimethylammonium cation, and furthermore the trimethylbenzylammonium cation, the triethylbenzylammonium cation and the trimethyl-2-hydroxyethylammonium cation.

Particularly preferred as salt formers are the ammonium cation and di- and trialkylammonium cations in which the alkyl radicals, independently of one another, are straight-chain or branched $C_1$–$C_6$-alkyl groups which are optionally substituted by a hydroxyl group, such as, for example, the dimethylammonium cation, the trimethylammonium cation, the triethylammonium cation, the di(2-hydroxyethyl) ammonium cation and the tri(2-hydroxyethyl)ammonium cation.

Compounds of the formula I or salts thereof which are of particular interest are those in which $R^2$ is hydrogen, $C_1-C_4$-alkyl, $C_1-C_4$-haloalkyl, $C_5-C_6$-cycloalkyl, benzyl, trimethylsilyl or triethylsilyl or in which $R^3$ is OR , $NR^8{}_2$, $S(O)_n-R^{10}$ or $OR^{10}$, in which n is 0, 1 or 2, and $R^7$, $R^8$ and $R^{10}$ have the abovementioned meanings, or in which, $R^4$ is hydrogen, $C_1-C_4$-alkyl, $C_1-C_4$-haloalkyl, $C_2-C_4$-alkenyl, $C_2-C_4$-alkynyl, $C_5-C_6$-cycloalkyl, benzyl or $OR^{11}$, in which $R^{11}$ has the abovementioned meaning, or $R^3$ and $R^4$ together are =O or a diradical of the formula $-SCH_2CH_2CH_2S-$, $-SCH_2CH_2S-$, $-OCH_2CH_2CH_2-O-$ or $-OCH_2CH_2HO-$, or in which $R^5$ and $R^6$ are identical or different radicals which, independently of one another, are hydrogen, halogen, nitro, cyano, amino or $C_1-C_4$-haloalkyl, $C_1-C_4$-haloalkoxy, $C_1-C_4$-alkyl, $C_1-C_4$-alkoxy, mono($C_1-C_4$-alkyl)amino, di($C_1-C_4$-alkyl)amino, $C_1-C_4$-alkylthio, $C_1-C_4$-alkylsulfonyl, or in which a combination of the above, preferred meanings exists.

Other compounds of the abovementioned formula I and salts thereof which are of particular interest are those in which R is hydrogen, $C_1-C_8$-alkyl, $C_4-C_7$-cycloalkyl, $C_2-C_8$-alkenyl or $C_2-C_8$-alkynyl, heterocyclyl, phenyl or heteroaryl, where each of the last-mentioned seven radicals, independently of one another, is unsubstituted or substituted by one or more radicals selected from the group comprising halogen, cyano, nitro, thio, hydroxyl, $C_1-C_4$-alkyl, $C_1-C_4$-haloalkyl, the latter two substituents only in the case of cyclic radicals, $C_1-C_4$-alkoxy, $C_2-C_4$-alkenyloxy, $C_2-C_4$-alkynyloxy, $C_1-C_4$-haloalkoxy, $C_1-C_4$-alkylthio, $C_2-C_4$-alkenylthio, $C_2-C_4$alkynylthio, $C_5-C_6$-cycloalkyl, $C_5-C_6$-cycloalkoxy, amino, mono- and di($C_1-C_4$-alkyl)amino, ($C_1-C_6$-alkoxy)carbonyl, radicals of the formulae $-SiR^d{}_3$, in which the $R^d$ radicals independently of one another are $C_1-C_4$-alkyl, benzyl or phenyl, and radicals of the formulae $-O-NR^e{}_2$, $-O-N=CR^e{}_2$, $-N=CR^e{}_2$, $-CH(OR^e)_2$, in which the $R^e$ radicals in the abovementioned formulae, independently of one another, are hydrogen, $C_1-C_4$-alkyl or phenyl, or, in pairs, are a $C_2-C_5$-alkylene chain, or compounds in which $R^*$ and $R^7$, independently of one another, are a radical of the formula $-CO-R$, $-NR^hR^i$ or $-N=CR^jR^k$, in which R, $R^h$, $R^i$, $R^j$ and $R^k$ have the abovementioned meanings.

Preferably,

R, $R^{10}$ and $R^{11}$, independently of one another, are hydrogen, $C_1-C_8$-alkyl, $C_5-C_6$-cycloalkyl, $C_2-C_8$-alkenyl or $C_2-C_8$-alkynyl, where each of the last-mentioned four radicals, independently of one another, is unsubstituted or substituted by one or more radicals selected from the group comprising halogen, cyano, nitro, $C_1-C_4$-alkoxy, $C_2-C_4$-alkenyloxy, $C_2-C_4$-alkynyloxy, $C_5-C_6$-cycloalkyl, $C_5-C_6$-cycloalkoxy, mono- and di($C_1-C_4$-alkyl)amino, radicals of the formulae $-SiR^d{}_3$, in which the $R^d$ radicals, independently of one another, are $C_1-C_2$-alkyl or phenyl, and radicals of the formulae $-O-N=CR^e{}_2$ and $-N=CR^e{}_2$, in which the $R^e$ radicals in the abovementioned formulae, independently of one another, are hydrogen, $C_1-C_2$-alkyl or phenyl, or, in pairs, are a $C_2-C_5$-alkylene chain, and $R^*$ and $R^7$, independently of one another, are preferably $-CO-R$, in which R has the abovementioned meaning, or $-NR^hR^i$ or $-N=CR^jR^k$, in which $R^h$ and $R^i$, independently of one another, are hydrogen, $C_1-C_2$-alkyl, benzyl or phenyl or, together with the nitrogen atom, are pyrrolidin-1-yl, piperidin-1-yl, morpholin-4-yl, piperazin-1-yl or imidazol-1-yl, or $R^j$ and $R^k$, independently of one another, are hydrogen, $C_1-C_2$-alkyl, benzyl or phenyl or, together, are a $C_4-C_5$-alkylene chain.

Other compounds of the abovementioned formula I and salts thereof which are of particular interest are those in which $R^8$ radicals independently of one another are hydrogen, $C_1-C_4$-alkyl, $C_1-C_4$-haloalkyl, $C_2-C_4$-alkenyl, $C_2-C_4$-alkynyl, $C_5-C_6$-cycloalkyl, benzyl or phenyl, Y is oxygen, $R^9$ radicals independently of one another are hydrogen, $C_1-C_4$-alkyl, $C_1-C_4$-haloalkyl, $C_2-C_4$-alkenyl, $C_2-C_4$-alkynyl, $C_5-C_6$-cycloalkyl, $C_1-C_4$-alkoxy, $C_1-C_4$-haloalkoxy, phenyl or phenoxy, $R^{12}$ radicals independently of one another are $C_1-C_4$-alkyl, $C_1-C_4$-haloalkyl, $C_2-C_4$-alkenyl, $C_2-C_4$-alkynyl, $C_5-C_6$-cycloalkyl, benzyl or phenyl.

Other compounds of the abovementioned formula I and salts thereof which are of particular interest are those in which Z is O, S or $NR^8$, preferably O or $NR^8$, Q is O, S or $NR^8$, preferably O, $X_i$ radicals independently of one another are O, S, $NR^8$ or $N-(A_iX_i)_q-R$, in which R and $R^8$ have the abovementioned meaning, $A_i$ radicals independently of one another are unsubstituted or substituted $C_1-C_4$-alkylene, $C_2-C_4$-alkenylene, or $C_5-C_6$-cycloalkylene, preferably $C_1-C_4$-alkylene, i is a consecutive number which, if q is unequal to 0, assumes the meaning of all integers from 1 to q, where q has the meaning given below, q is an integer from 0 to 4, the total of the numbers q being less than 6.

Preferred compounds of the formula I and salts thereof are those in which $R^1$ radicals are radicals of the formula

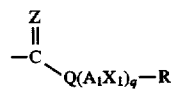

in which R, Z, Q, $A_i$, $X_i$ and q have the abovementioned meanings.

The invention also relates to a method of protecting crop plants, preferably maize, cereal or rice plants, against phytotoxic side-effects of herbicides, which comprises applying an effective amount of at least one compound of the formula I or a salt thereof either before, after or simultaneously with the abovementioned herbicidal active substance to the plants, the seeds of the plants or the area under cultivation.

The invention furthermore relates to the use of compounds of the formula I or salts thereof for protecting crop plants against phytotoxic side-effects of herbicides.

All other compounds of the formula I which are hitherto unknown are also part of the invention.

The compounds of the formula I can be prepared by generally known processes, see, for example Synthesis 1991, 625; EP-A-269046; Tetrahedron 44 (1988), 7213; Synthesis 1986, 403; J. Chem. Soc., Chem. Commun. 1987, 102; J. Chem. Soc., Chem. Commun. 1987, 1410; Org. Synth. Coll. Vol. III, 1955, 91; Ber. Deutsch. Chem. Ges. 87 (1954), 1189; Ber. Deutsch. Chem. Ges. 89 (1956), 1423; J. Amer. Chem. Soc. 108 (1986), 8112; J. Org. Chem. 23 (1958), 94; Tetrahedron Lett. 1970, 3147; J. Chem. Soc. Perkin Trans. I 1983, 2879; J. Org. Chem. 53 (1988), 4069; Zh. Obshch. Khimii 56 (1986), 2678; Zh. Obshch. Khimii 54 (1984), 69; Izv. An. SSSR Ser. Khim. 1980, 382, and the literature cited therein.

Thus, the compounds of the formula I according to the invention can be prepared in such a manner that, a) in the event that $R^3$ in formula I is $NR^8{}_2$, $OR^{10}$ or $SR^{10}$, a compound of the formula II

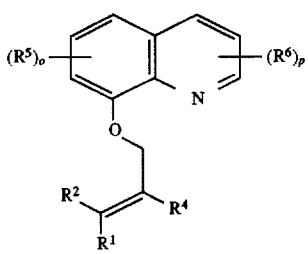

(II)

is reacted with a compound of the formula H—$NR^8{}_2$, H—$OR^{10}$ or H—$SR^{10}$, if appropriate in the presence of a base, $R^8$ and $R^{10}$ being defined as in the abovementioned formula (I), or, b) in the event that $R^3$ in formula I is $P(O)R^9{}_2$, a compound of the formula II

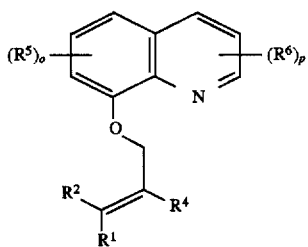

(II)

is reacted with a compound of the formula $P(OR)R^9{}_2$ or with a compound of the formula $PH(O)R^9{}_2$ in the presence of a base, $R^9$ being as defined in formula I and R being defined analogously to R in formula I, or, c) in the event that $R^3$ in formula I is $NR^8{}_2$, $OR^{10}$ or $SR^{10}$, a compound of the formula III

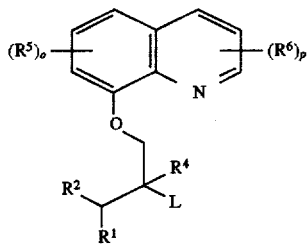

(III)

is reacted with a compound of the formula H—$NR^8{}_2$, H—$OR^{10}$ or H—$SR^{10}$, if appropriate in the presence of a base, where L is a leaving group such as, for example, chlorine, bromine, methanesulfonyl or toluenesulfonyl and $R^8$ and $R^{10}$ are defined as in the abovementioned formula I, or, d) in the event that $R^3$ in formula I is hydroxyl, a compound of the formula IV

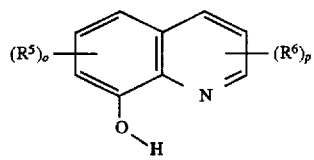

(IV)

is reacted with a compound of the formula V

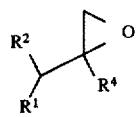

(V)

in the presence of a base, or e) in the event that $R^3$ in formula I is hydroxyl, a compound of the formula VI

(VI)

is reacted with a compound of the formula VII

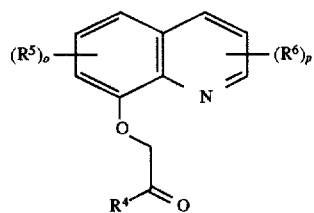

(VII)

in which M is a metal or metal halide, such as, for example Li, ZnBr or MgCl, or, f) in the event that $R^3$ in formula I is $S(O)_n$—$R^{10}$ and n is 1 or 2, a compound of the formula VIII

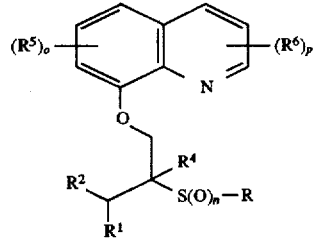

(VIII)

in which n is 0 or 1 and $R^{10}$ is defined as in the abovementioned formula I, is oxidized with an oxidant to give a compound VIII, which corresponds to the abovementioned compound VIII, but n is now greater and, as in formula I, is 1 or 2, or, g) in the event that $R^3$ and $R^4$ in formula I together are =O, a compound of the formula IX

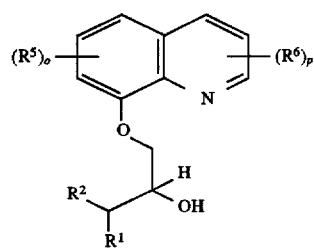

(IX)

is oxidized with an oxidant to give the compound of the formula X

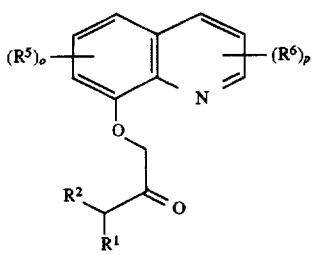

(X)

or, h) in the event that $R^3$ and $R^4$ in formula I together are a divalent radical of the formula —$Q^1$—A—$Q^2$—, in which A, $Q^1$ and $Q^2$ are defined as in formula I, a compound of the abovementioned formula (X) is reacted with a compound of the formula H—$Q^1$—A—$Q^2$—H, the symbols $R^1$, $R^2$, $R^3$, $R^4$, $R^5$, $R^6$, o and p in the above-mentioned formulae II, III, IV, V, VI, VII, VIII, IX and X of variants a) to h) being defined as in formula I.

The reactions in accordance with variant a) are preferably carried out in aprotic solvents, such as toluene, N,N-dimethylformamide, dimethyl sulfoxide, acetonitrile, methyl isobutyl ketone, acetone or dioxane, or in alcohols, such as methanol or ethanol, at ice-bath temperature up to elevated temperature, in particular between 0° and 150° C., if appropriate in the presence of a base, in particular alkali metal alcoholates, such as, for example, sodium methanolate or sodium ethanolate, or in multi-phase solvent mixtures, in particular mixtures of chlorinated hydrocarbons and water, in the presence of a phase transfer catalyst, in particular quaternary ammonium bases, and of a base, in particular alkali metal hydroxides, such as, for example, sodium hydroxide or potassium hydroxide, at ice-bath temperature up to elevated temperature, in particular between 0° and 100° C. The reactions in accordance with variant b) are preferably carried out in undiluted form or in aprotic solvents, such as toluene, diethyl ether, N,N-dimethylformamide, dimethyl sulfoxide, acetonitrile, methyl isobutyl ketone, acetone or dioxane, or in alcohols, such as methanol or ethanol, at ice-bath temperature up to elevated temperature, in particular between 0° C. and the boiling point of the solvent used, if appropriate in the presence of a base, in particular alkali metal alcoholates or alkali metal hydrides, such as, for example, sodium methanolate or sodium hydride. The reactions in accordance with variant c) are preferably carried out in aprotic solvents, such as toluene, N,N-dimethylformamide, dimethyl sulfoxide, acetonitrile, methyl isobutyl ketone, acetone or dioxane, at normal temperature up to elevated temperature, in particular between 20° and 180° C., if appropriate in the presence of a base, in particular alkali metal carbonates or alkali metal hydrides, such as, for example, potassium carbonate or sodium hydride. The reactions in accordance with variant d) are preferably carried out in aprotic solvents, such as toluene, N,N-dimethylformamide, dimethyl sulfoxide, acetonitrile, methyl isobutyl ketone, acetone or dioxane, at ice-bath temperature up to elevated temperature, in particular between 0° and 150° C., in the presence of a base, in particular alkali metal carbonates or alkali metal hydrides, such as, for example, potassium carbonate or sodium hydride. The reactions in accordance with variant e) are preferably carried out in aprotic solvents, in particular ethers, such as diethyl ether, tetrahydrofuran, dioxane, ethylene glycol dimethyl ether or diethylene glycol dimethyl ether, at cooling-bath temperature up to elevated temperature, in particular between −80° C. and the boiling point of the solvent used. The oxidations in accordance with variant f) are mainly carried out in such a manner that a compound of the formula VIII in which n is 0 or 1 is reacted with the stoichiometric amount of an inorganic oxidant, such as, for example, sodium periodate or potassium peroxomonosulfate (Oxone®), in a polar solvent or solvent mixture which contains, in particular, water, ethanol, acetone or acetic acid, at ice-bath temperature up to elevated temperature, in particular between 0° and 100° C. The reactions in accordance with variant g) are mainly carried out in such a manner that a compound of the formula IX is reacted with an oxidant, such as, for example, dimethyl sulfoxide/oxalyl chloride/triethylamine or Cr(VI) compounds, in aprotic solvents, in particular hydrocarbons or halogenated hydrocarbons, such as, for example, hexane, benzene or dichloromethane, or in polar solvents, such as acetone, acetic acid or water, at cooling bath temperature up to elevated temperature, in particular between −80° and 100° C. The reactions in accordance with variant h) are preferably carried out in aprotic solvents, in particular hydrocarbons or halogenated hydrocarbons, such as, for example, toluene, dichloromethane or chloroform, at ice-bath temperature up to elevated temperature, in particular between 0° and 100° C., in the presence of acidic catalysts, such as, for example, p-toluenesulfonic acid, boron trifluoride, or else zinc chloride.

Compounds of the formula I (hereinafter, compounds of the formula I are always also to be understood as including the salts thereof) reduce or prevent phytotoxic secondary effects of herbicides which may occur when the herbicides are used in crops of useful plants.

The compounds of the formula I according to the invention and the herbicidal active substances can be applied simultaneously or in succession, in any desired sequence, and are then capable of reducing, or completely compensating for, the harmful side-effects of these herbicides on crop plants without adversely affecting the efficacy of these herbicides against harmful plants.

This allows the field of application of conventional crop protection products to be widened considerably. Herbicides whose phytotoxic side-effects on crop plants can be reduced by means of compounds of the formula I are, for example, carbamates, thiocarbamates, haloacetanilides, substituted phenoxy-, naphthoxy- and phenoxyphenoxycarboxylic acid derivatives and heteroaryloxyphenoxyalkanecarboxylic acid derivatives, such as quinolyloxy-, quinoxalyloxy-, pyridyloxy-, benzoxalyloxy- and benzothiazolyloxyphenoxyalkanecarboxylic esters, cyclohexanedione derivatives, imidazolinones, pyrimidyloxypyridinecarboxylic acid derivatives, pyrimidyloxybenzoic acid derivatives, sulfonylureas and triazolopyrimidinesulfonamide derivatives. Preferred are the esters and salts of phenoxyphenoxy- and heteroaryloxyphenoxycarboxylic acid, or sulfonylureas and imidazolinones. Examples of suitable herbicides which can be combined with the safeners according to the invention are:

A) Herbicides of the ($C_1$–$C_4$)alkyl, ($C_2$–$C_4$)alkenyl and ($C_3$–$C_4$)alkynyl phenoxyphenoxy- and heteroaryloxyphenoxycarboxylates, such as A1) Phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy)propionate (see DE-A-2601548), methyl 2-(4-(4-bromo-2-fluorophenoxy)phenoxy)propionate (see U.S. Pat. No. 4,808,750), methyl 2-(4-(2-chloro-4-trifluoromethylphenoxy)phenoxy)propionate (see DE-A-2433067), methyl 2-(4-(2-fluoro-4-trifluoromethylphenoxy)phenoxy)propionate (see U.S. Pat. No. 4,808,750), methyl 2-(4-(2,4-dichlorobenzyl) phenoxy)propionate (see DE-A-2417487), ethyl 4-(4-(4-trifluoromethylphenoxy)phenoxy)pent-2-enoate, methyl 2-(4-(4-trifluoromethylphenoxy)phenoxy) propionate (see DE-A-2433067), butyl 2-(4-(4-cyano-2-fluorophenoxy)phenoxy)propionate (see EP-A-302203)

A2) "Mononuclear" heteroaryloxyphenoxyalkanecarboxylic acid derivatives, for example ethyl 2-(4-(3,5-dichloropyridyl-2-oxy)phenoxy)propionate (see EP-A-2925), propargyl 2-(4-(3,5-dichloropyridyl-2-oxy)phenoxy)propionate (EP-A-3114), methyl 2-(4-(3-chloro-5-trifluoromethyl-2-pyridyloxy) phenoxypropionate (see EP-A-3890), ethyl 2-(4-(3-chloro-5-trifluoromethyl-2-pyridyloxy)phenoxy) propionate (see EP-A-3890), propargyl 2-(4-(5-chloro-3-fluoro-2-pyridyloxy)phenoxy)propionate (EP-A-191736), butyl 2-(4-(5-trifluoromethyl-2-pyridyloxy) phenoxy)propionate (fluazifop-butyl), A3) "Binuclear" heteroaryloxyphenoxyalkanecarboxylic acid derivatives, for example methyl and ethyl 2-(4-(6-chloro-2-quinoxalyloxy)phenoxy)propionate (quizalofop-methyl and -ethyl), methyl 2-(4-(6-fluoro-2-quinoxalyloxy)phenoxy)propionate (see J. Pest. Sci. Vol. 10, 61 (1985)), 2-(4-(6-chloro-2-quinoxalyloxy) phenoxy)propionic acid and its 2-isopropylideneaminooxyethyl ester (propaquizafop and ester), ethyl 2-(4-(6-chlorobenzoxazol-2-yloxy) phenoxy)propionate (fenoxaprop-ethyl), its D(+) isomer (fenoxaprop-P-ethyl) and ethyl 2-(4-(6-chlorobenzothiazol-2-yloxy)phenoxypropionate (see DE-A-2640730), tetrahydrofur-2-ylmethyl 2-(4-(6-chloroquinoxalyloxy)phenoxypropionate (see EP-A 323 727), B) Herbicides from the sulfonylurea series, such as, for example, pyrimidinyl- or triazinylaminocarbonyl[benzene-, pyridine-, pyrazol-, thiophene- and (alkylsulfonyl) alkylamino]sulfamides. Preferred as substituents on the pyrimidine ring or triazine ring are alkoxy, alkyl, haloalkoxy, haloalkyl, halogen or dimethylamino, it being possible for all substituents to be combined independently of each other. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl, (alkanesulfonyl)alkylamino. Examples of suitable sulfonyl ureas are B1) Phenyl- and benzylsulfonylureas and related compounds, for example 1-(2-chlorophenylsulfonyl)-3-(4-methoxy-6-methyl-1,3,5-triazin-2-yl)urea (chlorsulfuron), 1-(2-ethoxycarbonylphenylsulfonyl)-3-(4-chloro-6-methoxypyrimidin-2-yl)urea (chlorimuron-ethyl), 1-(2-methoxyphenylsulfonyl)-3-(4-methoxy-6-methyl-1,3,5-triazin-2-yl)urea (metsulfuron-methyl), 1-(2-chloroethoxyphenylsulfonyl)-3-(4-methoxy-6-methyl-1,3,5-triazin-2-yl)urea (triasulfuron), 1-(2-methoxycarbonylphenylsulfonyl)-3-(4,6-dimethylpyrimidin-2-yl)urea (sulfometuron-methyl), 1-(2-methoxycarbonylphenylsulfonyl)-3-(4-methoxy-6-methyl-1,3,5-triazin-2-yl)-3-methylurea (tribenuron-methyl), 1-(2-methoxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis (difluoromethoxy)pyrimidin-2-yl)urea (primisulfuronmethyl), 3-(4-ethyl-6-methoxy-1,3,5-triazin-2-yl)-1-(2,3-dihydro-1,1-dioxo-2-methylbenzo[b]thiophene-7-sulfonyl)urea (see EP-A-79683), 3-(4-ethoxy-6-ethyl-1,3,5-triazin-2-yl)-1-(2,3-dihydro-1,1-dioxo-2-methylbenzo[b]thiophene-7-sulfonyl)urea (see EP-A-79683), B2) Thienylsulfonylureas, for example 1-(2-methoxycarbonylthiophen-3-yl)-3-(4-methoxy-6-methyl-1,3,5-triazin-2-yl)urea (thifensulfuron-methyl)

B3) Pyrazolylsulfonylureas, for example 1-(4-ethoxycarbonyl-1-methylpyrazol-5-ylsulfonyl)-3-(4,6-dimethoxypyrimidin-2-yl)urea (pyrazosulfuronmethyl), methyl 3-chloro-5-(4,6-dimethoxypyrimidin-2-ylcarbamoylsulfamoyl)-1-methylpyrazole-4-carboxylate (see EP 282613), methyl 5-(4,6-dimethylpyrimidin-2-ylcarbamoylsulfamoyl)-1-(2-pyridyl)pyrazole-4-carboxylate (NC-330, see Brighton Crop Prot. Conference—Weeds—1991, Vol. 1, 45 et seq.), B4) Sulfonediamide derivatives, for example 3-(4,6-dimethoxypyrimidin-2-yl)-1-(N-methyl-N-methylsulfonylaminosulfonyl)urea (amidosulfuron) and structural analogs (see EP-A-0131258 and Z. Pfl. Krankh. Pfl. Schutz 1990, Sonderheft XII, 489–497), B5) Pyridylsulfonylureas, for example 1-(3-N,N-dimethylaminocarbonylpyridin-2-ylsulfonyl)-3-(4,6-dimethoxypyrimidin-2-yl)urea (nicosulfuron), 1-(3-ethylsulfonylpyridin-2-ylsulfonyl)-3-(4,6-dimethoxypyrimidin-2-yl)urea (DPX-E 9636, see Brighton Crop Prot. Conf.—Weeds—1989, p. 23 et seq.), pyridylsulfonylureas, as they are described in DE-A-4000503 and DE-A-4030577; preferably those of the formula

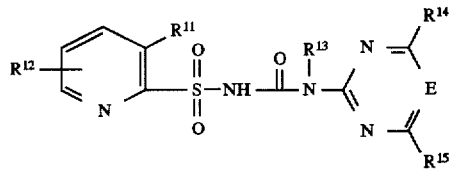

in which

E is CH or N, preferably CH, $R^{11}$ is iodine or $NR^{16}R^{17}$, $R^{12}$ is H, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy)-$C_1$–$C_3$-alkyl, ($C_1$–$C_3$-alkoxy) carbonyl, mono- or di($C_1$–$C_3$-alkyl)amino, $C_1$–$C_3$-alkylsulfinyl or -sulfonyl, $SO_2$—$NR^aR^b$ or CO—$NR^aR^b$, in particular H, $R^a$, $R^b$, independently of one another, are H, $C_3$–$C_3$-alkyl, $C_1$–$C_3$-alkenyl, $C_1$–$C_3$-alkynyl, or together are —$(CH_2)_4$—, —$(CH_2)_5$— or $(CH_2)_2$—O—$(CH_2)_2$—, $R^{13}$ is H or $CH_3$, $R^{14}$ is halogen, $C_1$–$C_2$-alkyl, $C_1$–$C_2$-alkoxy, $C_1$–$C_2$-haloalkyl, preferably $CF_3$, $C_1$–$C_2$-haloalkoxy, preferably $OCHF_2$ or $OCH_2CF_3$, $R^{15}$ is $C_1$–$C_2$-alkyl, $C_1$–$C_2$-haloalkoxy, preferably $OCHF_2$, or $C_1$–$C_2$-alkoxy, and $R^{16}$ is $C_1$–$C_4$-alkyl and $R^{17}$ is $C_1$–$C_4$-alkylsulfonyl, or $R^{16}$ and $R^{17}$ together are a chain of the formula —$(CH_2)_3$ $SO_2$— or —$(CH_2)_4SO_2$, for example 3-(4,6-dimethoxypyrimidin-2-yl)-1-(3-N-methylsulfonyl-N-methylaminopyridin-2-yl)sulfonylurea, or salts of these, B6) Alkoxyphenoxysulfonylureas, as they are described in EP-A-0342569, preferably those of the formula

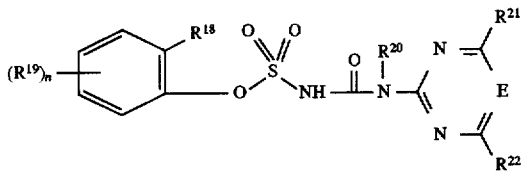

in which

E is CH or N, preferably CH, $R^{18}$ is ethoxy, propoxy or isopropoxy, $R^{19}$ is hydrogen, halogen, $NO_2$, $CF_3$, CN, $C_1$–$C_4$-alkyl, $C_1$–$C_4$-alkoxy, $C_1$–$C_4$-alkylthio or ($C_1$–$C_3$-alkoxy) carbonyl, preferably in the 6-position on the phenyl ring, n is 1, 2 or 3, preferably 1, $R^{20}$ is hydrogen, $C_1$–$C_4$-alkyl or $C_3$–$C_4$-alkenyl, $R^{21}$ and $R^{22}$, independently of one another, are halogen, $C_1$–$C_2$-alkyl, $C_1$–$C_2$-alkoxy, $C_1$–$C_2$-haloalkyl, $C_1$–$C_2$-haloalkoxy or ($C_1$–$C_2$-alkoxy)-$C_1$–$C_2$-alkyl, preferably $OCH_3$ or $CH_3$, for example 3-(4,6-dimethoxypyrimidin-2-yl)-1-(2-ethoxyphenoxy) sulfonylurea, or the salts of these, and other related sulfonylurea derivatives and mixtures of these, C) Chloroacetanilide herbicides, such as N-methoxymethyl-2,6-diethylchloroacetanilide (alachlor), N-(3'-methoxyprop-2'-yl)-2-methyl-6-ethylchloroacetanilide (metolachlor), -N-(3-methyl-1,2,4-oxadiazol-5-ylmethyl)chloroacetic acid 2,6-dimethylanilide N-(2,6-dimethylphenyl)-N-(1-pyrazolylmethyl) chloroacetamide (metazachlor), D) Thiocarbamates, such as S-ethyl N,N-dipropylthiocarbamate (EPTC) or S-ethyl N,N-diisobutylthiocarbamate (butylate), E) Cyclohexanedione derivatives, such as methyl 3-(1-allyloxyiminobutyl)-4-hydroxy-6,6-dimethyl-2-oxocyclohex-3-enecarboxylate (alloxydim), 2-(1-ethoximinobutyl)-5-(2-ethylthiopropyl)-3-hydroxycyclohex-2-en-1-one (sethoxydim), 2-(1-ethoximinobutyl)-5-(2-phenylthiopropyl)-3-hydroxycyclohex-2-en-1-one (cloproxydim), 2-(1-(3-chloroallyloxy)iminobutyl)-5-[2-(ethylthio)propyl]-3-hydroxycyclohex-2-en-1-one, 2-(1-(3-chloroallyloxy) iminopropyl)-5-[2-(ethylthio)propyl]-3-hydroxycyclohex-2-en-1-one (clethodim), 2-(1-(ethoxyimino)butyl)-3-hydroxy-5-(thian-3-yl)cyclohex-2-enone (cycloxydim), or 2-(1-ethoxyiminopropyl)-5-(2,4,6-trimethylphenyl)-3-hydroxycyclohex-2-en-1-one (tralkoxydim), F) 2-(4-alkyl-5-oxo-2-imidazolin-2-yl)benzoic acid derivatives or 2-(4-alkyl-5-oxo-2-imidazolin-2-yl) heteroarylcarboxylic acid derivatives, such as, for example, methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz), 5-ethyl-2-(4-isopropyl-4-methyl-5-oxo-2-imidazolin-2-yl) pyridine-3-carboxylic acid (imazethapyr), 2-(4-isopropyl-4-methyl-5-oxo-2-imidazolin-2-yl)quinoline-3-carboxylic acid (imazaquin), 2-(4-isopropyl-4-methyl-5-oxo-2-imidazolin-2-yl)pyridine-3-carboxylic acid (imazapyr), 5-methyl-2-(4-isopropyl-4-methyl-5-oxo-2-imidazolin-2-yl)pyridine-3-carboxylic acid (imazethamethapyr), G) Triazolopyrimidinesulfonamide derivatives, for example N-(2,6-difluorophenyl)-7-methyl-1,2,4-triazolo(1,5-c)pyrimidine-2-sulfonamide (flumetsulam), N-(2,6-dichloro-3-methylphenyl)-5,7-dimethoxy-1,2,4-triazolo(1,5-c)pyrimidine-2-sulfonamide, N-(2,6-difluorophenyl)-7-fluoro-5-methoxy-1,2,4-triazolo(1,5-c)pyrimidine-2-sulfonamide, N-(2,6-dichloro-3-methylphenyl)-7-chloro-5-methoxy-1,2,4-triazolo(1,5-c)pyrimidine-2-sulfonamide, N-(2-chloro-6-methoxycarbonyl)-5,7-dimethyl-1,2,4-triazolo(1,5-c)pyrimidine-2-sulfonamide, (see, for example, EP-A-343 752, U.S. Pat. No. 4,988,812), H) Benzoylcyclohexanedione derivatives, for example 2-(2-chloro-4-methylsulfonylbenzoyl)cyclohexane-1,3-dione (SC-0051, see EP-A-137 963), 2-(2-nitrobenzoyl)-4,4-dimethylcyclohexane-1,3-dione (see EP-A-274634), 2-(2-nitro-3-methylsulfonylphenyl)-4,4-dimethylcyclohexane-1,3-dione (see WO-91/13548), J) Pyrimidinyloxypyrimidinecarboxylic acid derivatives or pyrimidinyloxybenzoic acid derivatives, for example benzyl 3-(4,6-dimethoxypyrimidin-2-yl)oxypyridine-2-carboxylate (EP-A-249 707), methyl 3-(4,6-dimethoxypyrimidin-2-yl)oxypyridine-2-carboxylate (EP-A-249 707), 2,6-bis[(4,6-dimethoxypyrimidin-2-yl)oxy] benzoic acid (EP-A-321 846), 1-ethoxycarbonyloxyethyl 2,6-bis[(4,6-dimethoxypyrimidin-2-yl)oxy]benzoate (EP-A-472 113).

The abovementioned herbicides of groups A to J are known to the expert and, as a rule, described in "The Pesticide Manual", British Crop Protection Council, 9th Edition 1991 or 8th Edition 1987, or in "Agricultural Chemicals Book II, Herbicides", by W. T. Thompson, Thompson Publications, Fresno Calif., USA 1990 or in "Farm Chemicals Handbook '90", Meister Publishing Company, Willoughby Ohio, USA 1990. Imazethamethapyr is known from Weed Techn. 1991, Vol. 5, 430–438.

The herbicidal active substances and the abovementioned safeners can be applied together (as a finished formulation or by the tank mix method) or in any desired sequence one after the other. The ratio by weight of safener:herbicide can vary within wide limits and is preferably in the range of 1:10 to 10:1, in particular 1:10 to 5:1. The amounts of herbicide and safener which are optimal in each case will depend on the type of the herbicide used or on the safener used as well as on the nature of the plant stand to be treated and can be determined in each individual case by suitable preliminary experiments.

Main fields of application for the safeners are, especially, cereal crops (wheat, rye, barley, oats), rice, maize, sorghum, and also cotton and soya beans, preferably cereals, rice and maize.

The safeners of the formula I according to the invention are particularly advantageous when combined with herbicides from the group of the sulfonylureas and/or imidazolinones and also with herbicides of the phenoxyphenoxy- and heteroaryloxyphenoxyalkanecarboxylic acid type.

Some herbicides of these structural classes cannot be used selectively, or not selectively enough, in cereal crops and/or maize and also rice. The combination with the safeners according to the invention allows outstanding selectivity to be achieved in cereals, maize or rice even when these herbicides are used.

Depending on their properties, the safeners of the formula I can be used for pretreating the seed of the crop plant (seed dressing) or incorporated into the seed furrows before sowing or used together with the herbicide before or after emergence of the plants. Pre-emergence treatment includes the treatment of the area before sowing and the treatment of the areas under cultivation where seed has been sown, but which are still without vegetation cover. Preferred is the joint use together with the herbicide. To this end, tank mixes or readymixes can be employed.

Depending on the indication and the herbicide used, the application rates of said safener required vary within wide limits and are, as a rule, in the range of 0.001 to 5 kg, preferably 0.005 to 0.5 kg, of active substance per hectare.

The present invention therefore also relates to a method of protecting crop plants against phytotoxic side-effects of herbicides, which comprises applying an effective amount of a compound of the formula I before, after or simultaneously with the herbicide to the plants, the seeds of the plants or the area under cultivation.

The invention also relates to crop protection products which contain an active substance of the formula I and conventional formulation auxiliaries and to herbicidal compositions which contain an active substance of the formula I and a herbicide and formulation auxiliaries conventionally used in the field of crop protection.

For example, the compounds of the formula (I) according to the invention and their combinations with herbicides can be applied in the form of wettable powders, emulsifiable concentrates, sprayable solutions, dusts and granules in the customary preparations. The choice of a certain formulation will be determined by the application method desired and the prevailing biological and/or chemico-physical parameters, with optimization of the formulation components generally requiring systematic test series. Examples of types of formulations are wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes. These individual types of formulations are known in principle and described, for example, in: Winnacker-Küchler, "Chemische Technologie", [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries which are necessary, such as inert materials, surfactants, solvents and other additives are also known and described, for example, in: Watkins, "Handbook of Insecticide Dust Diluent and Carriers", 2nd Ed., Darland Books, Caldwell N.J., H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active substances, such as, for example, insecticides, acaricides, other herbicides, fungicides, safeners, fertilizers and/or growth regulators, for example in the form of a ready mix or a tank mix.

Wettable powders are preparations which are uniformly dispersible in water and which, besides the active substance, also contain ionic and/or non-ionic surfactants (wetting agents, dispersants), for example polyoxethylated alkylphenols, polyoxethylated fatty alcohols, polyoxethylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the active substances of the formula (I) and/or the combinations with herbicides are, for example, ground finely in customary apparatuses, such as hammer mills, blower mills and air-jet mills, and simultaneously or subsequently mixed with the formulation auxiliaries.

Emulsifiable concentrates are prepared by dissolving the active substance(s) in an organic solvent, for example butanol, cyclohexanone, dimethylformamide, xylene, or else higher-boiling aromatics or hydrocarbons or mixtures of the organic solvents, with an addition of one or more ionic and/or non-ionic surfactants (emulsifiers). Emulsifiers which can be used are, for example: calcium salts of alkylarylsulfonic acids, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as, for example, sorbitan fatty acid esters or polyoxyethylene sorbitan esters, such as, for example, polyoxyethylene sorbitan fatty acid esters.

Dusts are obtained by grinding the active substance(s) with finely-divided solid substances, for example talc, natural clays, such as kaolin, bentonite and pyrophyllite, or diatomaceous earth.

Suspension concentrates can be water- or oil-based. They can be prepared, for example, by wet grinding by means of commercially available bead mills, if appropriate with addition of surfactants as they have already been described for example above in the case of the other types of formulations.

Emulsions, for example oil-in-water emulsions (EW), can be prepared for example by means of stirrers, colloid mills and/or static mixers using aqueous organic solvents and, if appropriate, surfactants as they have already been described for example above in the case of the other types of formulations.

Granules can be prepared either by spraying the active substance onto adsorptive, granulated inert material or by applying active substance concentrates to the surface of carriers, such as sand, kaolinites or granulated inert material, with the aid of binders, for example polyvinyl alcohol, sodium polyacrylate or else mineral oils. Suitable active substances can also be granulated in the manner which is conventional for the production of fertilizer granules, if desired in the form of a mixture with fertilizers.

Water-dispersible granules are generally prepared by the customary processes, such as spray drying, fluidized-bed granulation, disk granulation, mixing with high-speed mixers and extrusion without solid inert material. For the preparation of disk granules, fluidized-bed granules, extruder granules and spray granules see, for example, the processes in "Spray-Drying Handbook" 3rd Ed. 1979, G. Goodwin Ltd., London, J. E. Browning, "Agglomeration", Chemical and Engineering 1967, pages 147 et seq.; "Perry's Chemical Engineer's Handbook", 5th Ed., McGraw-Hill, New York 1973, p. 8–57.

For more detailed information on the formulaton of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical preparations generally contain 0.1 to 99% by weight, in particular 0.1 to 95% by weight, of active substances of the formula I (antidote) or of the antidote/ herbicide active substance mixture and 1 to 99.9% by weight, in particular 5 to 99.8% by weight, of a solid or liquid additive and 0 to 25% by weight, in particular 0.1 to 25% by weight, of a surfactant.

In wettable powders, the concentration of active substance is, for example, approximately 10 to 90% by weight, the remainder to 100% by weight is composed of conventional formulation components. In the case of emulsifiable concentrates, the concentration of active substance can be approximately 1 to 90, preferably 5 to 80,% by weight. Formulations in the form of dusts contain 1 to 30, preferably in most cases 5 to 20,% by weight of active substance; sprayable solutions approximately 0.05 to 80, preferably 2 to 50,% by weight of active substance. In the case of water-dispersible granules, the active substance content depends partly on whether the active compound is in liquid or solid form and on which granulation auxiliaries, fillers and the like are used. In the case of the water-dispersible granules, the active substance content is, for example, between 1 and 95% by weight, preferably between 10 and 80% by weight.

Besides, the abovementioned formulations of active substance contain, if appropriate, the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules and sprayable solutions are conventionally not diluted any further with other inert substances prior to use. The application rate of the antidotes required will vary, inter alia, with the external conditions, such as temperature, humidity, and the nature of the herbicide used.

A) Formulation examples a) Dusts are obtained by mixing 10 parts by weight of a compound of the formula I or an active substance mixture of a herbicide and a compound of the formula I and 90 parts per weight of talc as inert substance and comminuting the mixture in a hammer mill.

b) A wettable powder which is readily dispersible in water is obtained by mixing 25 parts by weight of a compound of a formula I or of an active substance mixture of a herbicide and a safener of the formula I, 64 parts by weight of kaolin-containing quartz as inert substance, 10 parts by weight of potassium ligninsulfonate and 1 part by weight of sodium oleoylmethyltaurinate as wetting and dispersing agent and grinding the mixture in a pinned-disc mill.

c) A dispersion concentrate which is readily dispersible in water is obtained by mixing 20 parts by weight of a compound of the formula I or of an active substance mixture of a herbicide and a safener of the formula I, 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255° to above 277° C.), and grinding the mixture in a ball mill to a fineness of below 5 microns.

d) An emulsifiable concentrate is obtained from 15 parts by weight of a compound of the formula I or an active substance mixture of a herbicide and a safener of the formula I, 75 parts by weight of cyclohexanone as the solvent and 10 parts by weight of ethoxylated nonylphenol as the emulsifier.

e) Water-dispersible granules are obtained by mixing 75 parts by weight of a compound of the formula I or of an active substance mixture of a herbicide and a safener of the formula I, 10 " of calcium ligninsulfonate, 5 " of sodium lauryl sulfate, 3 " of polyvinyl alcohol and 7 " of kaolin, grinding the mixture in a pinned-disc mill and granulating the powder in a fluidized bed by spraying on water as the granulation liquid.

f) Water-dispersible granules are also obtained by homogenizing and precomminuting, on a colloid mill, 25 part(s) by weight of a compound of the formula I or of an active substance mixture of a herbicide and a safener of the formula I, 5 " of sodium 2,2'-dinaphthylmethane-6,6'-disulfonate, 2 " of sodium oleoylmethyltaurinate, 1 " of polyvinyl alcohol, 17 " of calcium carbonate, and 50 " of water, subsequently grinding the mixture in a bead mill and atomizing and drying the resulting suspension in a spray tower by means of a single-substance nozzle.

B. Preparation Examples

B1. Ethyl (RS)-4-(5-chloroquinoline-8-yloxy)-3-dimethylaminobutanoate (Table 1, Example 74)

A mixture of 5.8 g (20 mmol) of ethyl (E)-4-(5-chloroquinoline-8-yloxy)-2-butenoate, 20 ml of a 60% solution of dimethylamine in water and 0.34 g (1.0 mmol) of tetrabutylammonium hydrogen sulfate in 50 ml of dichloromethane, 40 ml of water and 10 ml of 2N sodium hydroxide solution was allowed to stand for two days at room temperature. The organic phase was separated off, and the aqueous phase was extracted twice using dichloromethane. After drying over magnesium sulfate, the solvent was stripped off in vacuo and the residue obtained was chromatographed on silica gel (ethyl acetate:heptane 7:3; followed by ethyl acetate). 1.0 g (15%) of the title compound was obtained as an oil.

B2. Ethyl (RS)-4-(5-bromoquinolin-8-yloxy)-3-ethylthiobutanoate (Table 1, Example 113)

A mixture of 1.0 g (3.0 mmol) of ethyl (E)-4-(5-bromoquinolin-8-yloxy)-2-butenoate, 0.2 g (3.3 mmol) of ethylmercaptan and 0.5 g of tetrabutylammonium hydrogen sulfate in 30 ml of dichloromethane, 25 ml of water and 10 ml of 2N sodium hydroxide solution was stirred for 16 hours at room temperature. The organic phase was separated off, the aqueous phase was extracted twice using dichloromethane, and the combined organic phases were washed using saturated ammonium chloride solution. After drying over magnesium sulfate, the solvent was stripped off in vacuo, and the residue obtained was chromatographed on silica gel (petroleum ether:ethyl acetate 1:1). 1.1 g (93%) of the title compound were obtained as an oil.

B3. Ethyl (RS)-4-(5-chloroquinolin-8-yloxy)-3-phenylthiobutanoate (Table 1, Example 206)

A mixture of 3.0 g (10.3 mmol) of ethyl (E)-4-(5-chloroquinolin-8-yloxy)-2-butenoate, 1.2 g (11.3 mmol) of thiophenol and 1.1 g (11.3 mmol) of triethylamine in 20 ml of chloroform was refluxed for 6 hours. The reaction mixture was subsequently washed using saturated ammonium chloride solution and saturated sodium chloride solution, and dried over magnesium sulfate, and the solvent was removed in vacuo. Column chromatography on silica gel (petroleum ether:ethyl acetate 2:1) gave 2.3 g (56%) of the title compound as an oil.

B4. Ethyl (RS)-4-(5-chloroquinolin-8-yloxy)-3-propylsulfonylbutanoate (Table 1, Example 146)

2.02 g (5.49 mmol) of ethyl (RS)-4-(5-chloroquinolin-8-yloxy)-3-propylthiobutanoate in 20 ml of ethanol were added dropwise with stirring at room temperature to 5.0 g (8.1 mmol) of potassium peroxomonosulfate (Oxone®) in a mixture of 20 ml of water and 20 ml of glacial acetic acid. The mixture was stirred for 16 hours at room temperature, 40 ml of water were added, the reaction mixture was extracted three times using ethyl acetate and the combined organic phases were washed using saturated sodium carbonate solution and dried over magnesium sulfate. The residue obtained after evaporation of the solvent in vacuo was purified by column chromatography on silica gel (petroleum ether:ethyl acetate 4:1 to 2:1). 2.07 g (94%) of the title compound were obtained as a yellow resin.

Table 1 below which follows lists the abovementioned preparation examples B1 to B4 together with other examples of compounds of the formula I which are prepared analogously. The following abbreviations are used in Table 1:

a) In the case of alkyl radicals and derivatives, such as alkoxy and the like:

n-, i-, s-, t- and c-alkyl is straight-chain, iso-, secondary, tertiary or cyclic alkyl.

b) In the case of phenyl radicals:

Ph=phenyl (or $C_6H_5$); o-, m- and p-=ortho-, meta- or para-substituted phenyl c) Bzl=benzyl

TABLE 1

(I)

| Ex. | $R^1$ | $R^2$ | $R^3$ | $R^4$ | $(R^5)_o$ | $(R^6)_p$ | M.p. [°C.] ($n_D^{30}$) |
|---|---|---|---|---|---|---|---|
| 1 | COOH | H | OH | H | H | H | |
| 2 | COOH | H | OH | H | 5-Cl | H | |
| 3 | COOH | $C_2H_5$ | OH | H | H | H | |
| 4 | COOCH$_3$ | H | OH | H | H | H | |
| 5 | COOCH$_3$ | H | OH | H | 5-Cl | H | |
| 6 | COOC$_2$H$_5$ | H | OH | H | H | H | |
| 7 | COOC$_2$H$_5$ | H | OH | H | 5-Cl | H | |
| 8 | COOC$_2$H$_5$ | H | OH | H | 5-Br | H | |
| 9 | COOH | H | O—CH$_3$ | H | H | H | |
| 10 | COOC$_2$H$_5$ | H | O—CH$_3$ | H | H | H | |
| 11 | COOH | H | O—CH$_3$ | H | 5-Cl | H | |
| 12 | COOC$_2$H$_5$ | H | O—CH$_3$ | H | 5-Cl | H | |
| 13 | COOC$_2$H$_5$ | H | O—CH$_3$ | H | 5-Cl | 2-CH$_3$ | |
| 14 | COOC$_2$H$_5$ | H | O—CH$_3$ | H | 5-Br | H | |
| 15 | COOC$_2$H$_5$ | H | O—CH$_3$ | H | H | H | |
| 16 | COOH | H | O—C$_2$H$_5$ | H | 5-Cl | H | |
| 17 | COOC$_2$H$_5$ | H | O—C$_2$H$_5$ | H | 5-Cl | H | |
| 18 | COOC$_2$H$_5$ | CH$_3$ | O—C$_2$H$_5$ | H | 5-Cl | H | |
| 19 | COOC$_2$H$_5$ | H | O—C$_2$H$_5$ | H | 5-Cl | 2-CH$_3$ | |
| 20 | COOC$_2$H$_5$ | H | O—C$_2$H$_5$ | H | 5-NO$_2$ | H | |
| 21 | COOC$_2$H$_5$ | H | O—C$_2$H$_5$ | H | 5-Br | H | |
| 22 | COOC$_2$H$_5$ | H | O—C$_3$H$_7$ | H | 5-Cl | H | |
| 23 | COOC$_2$H$_5$ | H | O—CH(CH$_3$)$_2$ | H | 5-Cl | H | |
| 24 | COOC$_2$H$_5$ | H | O—CH$_2$CH=CH$_2$ | H | 5-Cl | H | |
| 25 | COOC$_2$H$_5$ | H | O-n-C$_4$H$_9$ | H | 5-Cl | H | |
| 26 | COOC$_2$H$_5$ | H | O-i-C$_4$H$_9$ | H | 5-Cl | H | |
| 27 | COOC$_2$H$_5$ | H | O-s-C$_4$H$_9$ | H | 5-Cl | H | |
| 28 | COOC$_2$H$_5$ | H | O-t-C$_4$H$_9$ | H | 5-Cl | H | |
| 29 | COOC$_2$H$_5$ | H | O-n-C$_5$H$_{11}$ | H | 5-Cl | H | |
| 30 | COOC$_2$H$_5$ | H | O-n-C$_6$H$_{13}$ | H | 5-Cl | H | |
| 31 | COOC$_2$H$_5$ | H | O-n-C$_{12}$H$_{25}$ | H | 5-Cl | H | |
| 32 | COOC$_2$H$_5$ | H | O-c-C$_6$H$_{11}$ | H | 5-Cl | H | |
| 33 | COOC$_2$H$_5$ | H | O—CH$_2$C$_6$H$_5$ | H | 5-Cl | H | |
| 34 | COOC$_2$H$_5$ | H | O—C$_6$H$_5$ | H | 5-Cl | H | |
| 35 | COOC$_2$H$_5$ | H | O-p-C$_6$H$_4$—Cl | H | 5-Cl | H | |
| 36 | COOC$_2$H$_5$ | H | O—CH$_2$CH$_2$COOC$_2$H$_5$ | H | 5-Cl | H | |
| 37 | COOC$_2$H$_5$ | H | O—CH$_2$CH$_2$—OH | H | 5-Cl | H | |
| 38 | COOC$_2$H$_5$ | H | O—CH$_2$CH$_2$—OC$_2$H$_5$ | H | 5-Cl | H | |
| 39 | COOC$_2$H$_5$ | H | O—CO—CH$_3$ | H | 5-Cl | H | |
| 40 | COOC$_2$H$_5$ | CH$_3$ | O—CO—CH$_3$ | H | 5-Cl | H | |
| 41 | COOCH$_3$ | H | O—CO—C$_6$H$_5$ | H | 5-Cl | H | |
| 42 | COOH | H | =O | | H | H | |
| 43 | COOH | H | =O | | 5-Cl | H | |
| 44 | COOCH$_3$ | H | =O | | 5-Cl | H | |
| 45 | COOCH$_3$ | H | =O | | 5-Cl | 2-CH$_3$ | |
| 46 | COOC$_2$H$_5$ | H | =O | | 5-Cl | H | |

TABLE 1-continued

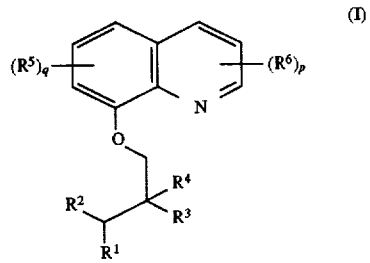

(I)

| Ex. | R¹ | R² | R³ | R⁴ | (R⁵)$_q$ | (R⁶)$_p$ | M.p. [°C.] (n$_D^{30}$) |
|---|---|---|---|---|---|---|---|
| 47 | COOC$_2$H$_5$ | CH$_3$ | | =O | 5-Cl | H | |
| 48 | COOC$_2$H$_5$ | H | | =O | 5-Br | H | |
| 49 | COOC$_2$H$_5$ | H | | =O | 5-NO$_2$ | H | |
| 50 | COOH | H | OCH$_3$ | OCH$_3$ | H | H | |
| 51 | COOCH$_3$ | H | OCH$_3$ | OCH$_3$ | H | H | |
| 52 | COOCH$_3$ | H | OCH$_3$ | OCH$_3$ | 5-Cl | H | |
| 53 | COOH | H | OC$_2$H$_5$ | OC$_2$H$_5$ | 5-Cl | H | |
| 54 | COOCH$_3$ | H | OC$_2$H$_5$ | OC$_2$H$_5$ | 5-Cl | H | |
| 55 | COOH | H | SCH$_3$ | SCH$_3$ | H | H | |
| 56 | COOH | H | SCH$_3$ | SCH$_3$ | 5-Cl | H | |
| 57 | COOC$_2$H$_5$ | H | SCH$_3$ | SCH$_3$ | 5-Cl | H | |
| 58 | COOC$_2$H$_5$ | H | SCH$_3$ | SCH$_3$ | 5-CF$_3$ | H | |
| 59 | COOH | H | SC$_2$H$_5$ | SC$_2$H$_5$ | H | H | |
| 60 | COOH | H | SC$_2$H$_5$ | SC$_2$H$_5$ | 5-Cl | H | |
| 61 | COOC$_2$H$_5$ | H | SC$_2$H$_5$ | SC$_2$H$_5$ | H | H | |
| 62 | COOH | H | —SCH$_2$CH$_2$CH$_2$S— | | H | H | |
| 63 | COOC$_2$H$_5$ | H | —SCH$_2$CH$_2$CH$_2$S— | | 5-Cl | H | |
| 64 | COOH | H | —SCH$_2$CH$_2$S— | | H | H | |
| 65 | COOH | H | —SCH$_2$CH$_2$S— | | 5-Cl | H | |
| 66 | COOC$_2$H$_5$ | H | —SCH$_2$CH$_2$S— | | 5-Cl | H | |
| 67 | COOH | H | NH$_2$ | H | H | H | |
| 68 | COOH | H | NH$_2$ | H | 5-Cl | H | |
| 69 | COOCH$_3$ | H | NH$_2$ | H | 5-Cl | H | |
| 70 | COOC$_2$H$_5$ | H | NH$_2$ | H | 5-Cl | H | |
| 71 | COOCH$_3$ | H | NH—CH$_3$ | H | 5-Cl | H | |
| 72 | COOCH$_3$ | H | N(CH$_3$)$_2$ | H | 5-Cl | H | |
| 73 | COOC$_2$H$_5$ | H | NH—CH$_3$ | H | 5-Cl | H | |
| 74 | COOC$_2$H$_5$ | H | N(CH$_3$)$_2$ | H | 5-Cl | H | (1.5622) |
| 75 | COOCH$_3$ | H | NH—C$_6$H$_{13}$ | H | 5-Cl | H | |
| 76 | COOCH$_3$ | H | NH—C$_6$H$_5$ | H | 5-Cl | H | |
| 77 | COOCH$_3$ | H | N(Bzl)$_2$ | H | 5-Cl | H | |
| 78 | COOCH$_3$ | H | N-piperidyl | H | 5-Cl | H | |
| 79 | COOC$_2$H$_5$ | H | N-morpholinyl | H | 5-Cl | H | |
| 80 | COOCH$_3$ | H | N(CH$_3$)OCH$_3$ | H | 5-Cl | H | |
| 81 | COOH | H | PO(OCH$_3$)$_2$ | H | H | H | |
| 82 | COOCH$_3$ | H | PO(OCH$_3$)$_2$ | H | H | H | |
| 83 | COOCH$_3$ | H | PO(OCH$_3$)$_2$ | H | 5-Cl | H | |
| 84 | COOC$_2$H$_5$ | H | PO(OC$_2$H$_5$)$_2$ | H | H | H | |
| 85 | COOC$_2$H$_5$ | H | PO(OC$_2$H$_5$)$_2$ | H | 5-Cl | H | |
| 86 | COOC$_2$H$_5$ | H | PO(CH$_3$)$_2$ | H | 5-Cl | H | |
| 87 | COOC$_2$H$_5$ | H | PO(C$_2$H$_5$)$_2$ | H | 5-Cl | H | |
| 88 | COOC$_2$H$_5$ | H | PO(C$_6$H$_5$)$_2$ | H | 5-Cl | H | |
| 89 | COOC$_2$H$_5$ | H | PS(C$_6$H$_5$)$_2$ | H | 5-Cl | H | |
| 90 | COOC$_2$H$_5$ | H | PO(CH$_3$)OCH$_3$ | H | 5-Cl | H | |
| 91 | COOC$_2$H$_5$ | H | PO(CH$_3$)OC$_2$H$_5$ | H | 5-Cl | H | |
| 92 | COOH | H | SH | H | H | H | |
| 93 | COOH | H | SH | H | 5-Cl | H | |
| 94 | COOCH$_3$ | H | SH | H | 5-Cl | H | |
| 95 | COOC$_2$H$_5$ | H | SH | H | 5-NO$_2$ | H | |
| 96 | COOC$_2$H$_5$ | CH$_3$ | SH | H | 5-Cl | H | |
| 97 | COOH | H | S—CH$_3$ | H | H | H | |
| 98 | COOCH$_3$ | H | S—CH$_3$ | H | 5-Cl | H | |
| 99 | COOCH$_3$ | H | SO—CH$_3$ | H | 5-Cl | H | |
| 100 | COOCH$_3$ | H | SO$_2$—CH$_3$ | H | 5-Cl | H | |
| 101 | COOCH$_3$ | H | S—CH$_3$ | H | 5-Br | H | |
| 102 | COOC$_2$H$_5$ | CH$_3$ | S—CH$_3$ | H | H | H | |
| 103 | COOC$_2$H$_5$ | H | S—CH$_3$ | H | 5-Cl | H | (1.5792) |
| 104 | COOC$_2$H$_4$ | H | S—CH$_3$ | H | 5-Br | H | |
| 105 | COOH | H | S—C$_2$H$_5$ | H | H | H | |
| 106 | COOH | H | SO—C$_2$H$_5$ | H | H | H | |
| 107 | COOH | H | SO$_2$—C$_2$H$_5$ | H | H | H | |
| 108 | COOH | H | S—C$_2$H$_5$ | H | 5-Cl | H | |
| 109 | COOCH$_3$ | H | S—C$_2$H$_5$ | H | 5-Cl | H | |

TABLE 1-continued (I)

| Ex. | $R^1$ | $R^2$ | $R^3$ | $R^4$ | $(R^5)_o$ | $(R^6)_p$ | M.p. [°C.] ($n_D^{30}$) |
|---|---|---|---|---|---|---|---|
| 110 | $COOC_2H_5$ | H | $S-C_2H_5$ | H | 5-Cl | H | oil |
| 111 | $COOC_2H_5$ | H | $SO-C_2H_5$ | H | 5-Cl | H | |
| 112 | $COOC_2H_5$ | H | $SO_2-C_2H_5$ | H | 5-Cl | H | 95–97 |
| 113 | $COOC_2H_5$ | H | $S-C_2H_5$ | H | 5-Br | H | oil |
| 114 | $COOC_2H_5$ | H | $SO-C_2H_5$ | H | 5-Br | H | |
| 115 | $COOC_2H_5$ | H | $SO_2-C_2H_5$ | H | 5-Br | H | |
| 116 | $COOCH_2CF_3$ | H | $S-C_2H_5$ | H | 5-Cl | H | |
| 117 | $COOCH(CH_3)(CH_2)_4CH_3$ | H | $S-C_2H_5$ | H | 5-Cl | H | |
| 118 | $COOC_6H_5$ | H | $S-C_2H_5$ | H | 5-Cl | H | |
| 119 | $COOC_2H_5$ | $CH_3$ | $S-C_2H_5$ | H | 5-Cl | H | |
| 120 | $COOC_2H_5$ | H | $S-C_2H_5$ | $CH_3$ | 5-Cl | H | |
| 121 | $COOC_2H_5$ | H | $S-C_2H_5$ | H | 5-Cl | 2-$CH_3$ | |
| 122 | $COOC_3H_7$ | H | $S-C_2H_5$ | H | 5-Cl | H | |
| 123 | COOH | H | $S$-n-$C_3H_7$ | H | H | H | |
| 124 | COOH | H | $SO$-n-$C_3H_7$ | H | H | H | |
| 125 | COOH | H | $SO_2$-n-$C_3H_7$ | H | H | H | |
| 126 | COOH | H | $S$-n-$C_3H_7$ | H | 5-Cl | H | |
| 127 | COOH | H | $S$-n-$C_3H_7$ | H | 5-Br | H | |
| 128 | COOH | H | $S$-n-$C_3H_7$ | H | 5-$CF_3$ | H | |
| 129 | COOH | H | $S$-n-$C_3H_7$ | H | 5-$NO_2$ | H | |
| 130 | COOH | H | $S$-n-$C_3H_7$ | H | 5-Cl | 2-$CH_3$ | |
| 131 | COOH | H | $S$-n-$C_3H_7$ | H | 5-CH(OH)$CCl_3$ | H | |
| 132 | $COOCH_3$ | H | $S$-n-$C_3H_7$ | H | H | H | |
| 133 | $COOCH_3$ | H | $S$-n-$C_3H_7$ | H | 5-Cl | H | |
| 134 | $COOCH_3$ | H | $S$-n-$C_3H_7$ | H | 5-Br | H | |
| 135 | $COOCH_3$ | H | $S$-n-$C_3H_7$ | H | 5-$CF_3$ | H | |
| 136 | $COOCH_3$ | H | $SO$-n-$C_3H_7$ | H | 5-$CF_3$ | H | |
| 137 | $COOCH_3$ | H | $SO_2$-n-$C_3H_7$ | H | 5-$CF_3$ | H | |
| 138 | $COOCH_3$ | H | $S$-n-$C_3H_7$ | H | 5-$NO_2$ | H | |
| 139 | $COOCH_3$ | H | $S$-n-$C_3H_7$ | H | 5-Cl | 2-$CH_3$ | |
| 140 | $COOCH_3$ | $CH_3$ | $S$-n-$C_3H_7$ | H | 5-Cl | H | |
| 141 | $COOCH_3$ | Bzl | $S$-n-$C_3H_7$ | H | 5-Cl | H | |
| 142 | $COOCH_3$ | H | $S$-n-$C_3H_7$ | H | 5-CH(OH)$CCl_3$ | H | |
| 143 | $COOC_2H_5$ | H | $S$-n-$C_3H_7$ | H | H | H | |
| 144 | $COOC_2H_5$ | H | $S$-n-$C_3H_7$ | H | 5-Cl | H | 45 |
| 145 | $COOC_2H_5$ | H | $SO$-n-$C_3H_7$ | H | 5-Cl | H | oil |
| 146 | $COOC_2H_5$ | H | $SO_2$-n-$C_3H_7$ | H | 5-Cl | H | resin |
| 147 | $COOC_2H_5$ | H | $S$-n-$C_3H_7$ | H | 5-Br | H | |
| 148 | $COOC_2H_5$ | H | $S$-n-$C_3H_7$ | H | 5-$CF_3$ | H | |
| 149 | $COOC_2H_5$ | H | $S$-n-$C_3H_7$ | H | 5-$CF_3$ | 2-$CH_3$ | |
| 150 | $COOC_2H_5$ | H | $S$-n-$C_3H_7$ | H | 5-$NO_2$ | H | |
| 151 | $COOC_2H_5$ | H | $S$-n-$C_3H_7$ | H | 5-Cl | 2-$CH_3$ | |
| 152 | $COOC_2H_5$ | H | $SO$-n-$C_3H_7$ | H | 5-Cl | 2-$CH_3$ | |
| 153 | $COOC_2H_5$ | H | $SO_2$-n-$C_3H_7$ | H | 5-Cl | 2-$CH_3$ | |
| 154 | $COOC_2H_5$ | H | $S$-n-$C_3H_7$ | $CH_3$ | 5-Cl | H | |
| 155 | $COOC_2H_5$ | $CH_3$ | $S$-n-$C_3H_7$ | H | 5-Cl | H | |
| 156 | $COOC_2H_5$ | $CH_3$ | $SO$-n-$C_3H_7$ | H | 5-Cl | H | |
| 157 | $COOC_2H_5$ | $CH_3$ | $SO_2$-n-$C_3H_7$ | H | 5-Cl | H | |
| 158 | $COOC_2H_5$ | Bzl | $S$-n-$C_3H_7$ | H | 5-Cl | H | |
| 159 | $COOCH_2CF_3$ | H | $S$-n-$C_3H_7$ | H | 5-Cl | H | |
| 160 | $COOC_3H_7$ | H | $S$-n-$C_3H_7$ | H | 5-Cl | H | |
| 161 | $COO$-n-$C_4H_9$ | H | $S$-n-$C_3H_7$ | H | 5-Cl | H | |
| 162 | $COO$-t-$C_4H_9$ | H | $S$-n-$C_3H_7$ | H | 5-Cl | H | |
| 163 | $COOCH_2C_6H_5$ | H | $S$-n-$C_3H_7$ | H | 5-Cl | H | |
| 164 | $COOCH(CH_3)(CH_2)_4CH_3$ | H | $S$-n-$C_3H_7$ | H | 5-Cl | H | |
| 165 | $COOCH_3$ | H | $S$-n-$C_3H_7$ | H | 5-CH(OH)$CCl_3$ | H | |
| 166 | COOH | H | $S-CH_2CH=CH_2$ | H | H | H | |
| 167 | COOH | H | $S-CH(CH_3)_2$ | H | H | H | |
| 168 | COOH | H | $S-CH(CH_3)_2$ | H | 5-Cl | H | |
| 169 | COOH | H | $S-CH(CH_3)_2$ | H | 5-$CF_3$ | H | |
| 170 | $COOCH_3$ | H | $S-CH(CH_3)_2$ | H | 5-Cl | H | |
| 171 | $COOC_2H_5$ | H | $S-CH(CH_3)_2$ | H | 5-Cl | H | oil |
| 172 | COOH | H | $S-CH_2CH=CH_2$ | H | 5-$CF_3$ | H | |

TABLE 1-continued

Structure (I): quinoline with $(R^5)_q$ and $(R^6)_p$ substituents, 8-position linked via $-O-CH_2-C(R^3)(R^4)-CH(R^2)-R^1$

| Ex. | $R^1$ | $R^2$ | $R^3$ | $R^4$ | $(R^5)_o$ | $(R^6)_p$ | M.p. [°C.] ($n_D^{30}$) |
|---|---|---|---|---|---|---|---|
| 173 | COOH | H | S—CH$_2$CH=CH$_2$ | H | 5-Cl | H | |
| 174 | COOH | H | SO—CH$_2$CH=CH$_2$ | H | 5-Cl | H | |
| 175 | COOH | H | SO$_2$—CH$_2$CH=CH$_2$ | H | 5-Cl | H | |
| 176 | COOH | H | S—CH$_2$CH=CH$_2$ | H | 5-Br | H | |
| 177 | COOCH$_3$ | H | S—CH$_2$CH=CH$_2$ | H | H | H | |
| 178 | COOCH$_3$ | H | S—CH$_2$CH=CH$_2$ | H | 5-Cl | H | |
| 179 | COOCH$_3$ | H | S—CH$_2$CH=CH$_2$ | H | H | H | |
| 180 | COOC$_2$H$_5$ | H | S—CH$_2$CH=CH$_2$ | H | 5-CF$_3$ | H | |
| 181 | COOC$_2$H$_5$ | H | S—CH$_2$CH=CH$_2$ | H | 5-Cl | H | oil |
| 182 | COOC$_2$H$_5$ | H | SO—CH$_2$CH=CH$_2$ | H | 5-Cl | H | |
| 183 | COOC$_2$H$_5$ | H | SO$_2$—CH$_2$CH=CH$_2$ | H | 5-Cl | H | 96–100 |
| 184 | COOC$_2$H$_5$ | H | S—CH$_2$CH=CH$_2$ | H | 5-Br | H | |
| 185 | COOC$_2$H$_5$ | H | SO—CH$_2$CH=CH$_2$ | H | 5-Br | H | |
| 186 | COOC$_2$H$_5$ | H | SO$_2$—CH$_2$CH=CH$_2$ | H | 5-Br | H | |
| 187 | COOC$_2$H$_5$ | H | S—CH$_2$CH=CH$_2$ | H | 5-Cl | 2-CH$_3$ | |
| 188 | COOC$_2$H$_5$ | CH$_3$ | S—CH$_2$CH=CH$_2$ | H | 5-CF$_3$ | H | |
| 189 | COOC$_3$H$_7$ | H | S—CH$_2$CH=CH$_2$ | H | 5-Cl | H | |
| 190 | COOC$_3$H$_7$ | H | S—CH$_2$CH=CH$_2$ | H | 5-CF$_3$ | H | |
| 191 | COO-n-C$_4$H$_9$ | H | S—CH$_2$CH=CH$_2$ | H | 5-Cl | H | |
| 192 | COO-t-C$_4$H$_9$ | H | S—CH$_2$CH=CH$_2$ | H | 5-Cl | H | |
| 193 | COOH | H | S-n-C$_4$H$_9$ | H | 5-Cl | H | |
| 194 | COOC$_2$H$_5$ | H | S-n-C$_4$H$_9$ | H | 5-Cl | H | |
| 195 | COOC$_2$H$_5$ | H | SO-n-C$_4$H$_9$ | H | 5-Cl | H | |
| 196 | COOC$_2$H$_5$ | H | SO$_2$-n-C$_4$H$_9$ | H | 5-Cl | H | |
| 197 | COOC$_2$H$_5$ | H | S-t-C$_4$H$_9$ | H | 5-Cl | H | 86–88 |
| 198 | COOC$_2$H$_5$ | H | S-s-C$_4$H$_9$ | H | 5-Cl | H | |
| 199 | COOC$_2$H$_5$ | H | S-i-C$_4$H$_9$ | H | 5-Cl | H | |
| 200 | COOC$_2$H$_5$ | H | S-n-C$_5$H$_{11}$ | H | 5-Cl | H | (1.5561) |
| 201 | COOC$_2$H$_5$ | H | S-n-C$_6$H$_{13}$ | H | 5-Cl | H | oil |
| 202 | COOC$_2$H$_5$ | H | S-c-C$_6$H$_{11}$ | H | 5-Cl | H | |
| 203 | COOC$_2$H$_5$ | H | S-n-C$_7$H$_{15}$ | H | 5-Cl | H | |
| 204 | COOC$_2$H$_5$ | H | S-n-C$_{12}$H$_{25}$ | H | 5-Cl | H | |
| 205 | COOC$_2$H$_5$ | H | S—CH$_2$—C$_6$H$_5$ | H | 5-Cl | H | 51 |
| 206 | COOC$_2$H$_5$ | H | S—C$_6$H$_5$ | H | 5-Cl | H | (1.6003) |
| 207 | COOC$_2$H$_5$ | H | S-p-C$_6$H$_4$—Cl | H | 5-Cl | H | |
| 208 | COOC$_2$H$_5$ | H | S-p-C$_6$H$_4$—Br | H | 5-Cl | H | |
| 209 | COOC$_2$H$_5$ | H | S-o-C$_6$H$_4$—Cl | H | 5-Cl | H | |
| 210 | COOC$_2$H$_5$ | H | S-(2,4-C$_6$H$_4$Cl$_2$) | H | 5-Cl | H | |
| 211 | COOC$_2$H$_5$ | H | S—CH$_2$CH$_2$C$_6$H$_5$ | H | 5-Cl | H | |
| 212 | COOC$_2$H$_5$ | H | S—CH$_2$COOC$_2$H$_5$ | H | 5-Cl | H | oil |
| 213 | COOC$_2$H$_5$ | H | SO—CH$_2$COOC$_2$H$_5$ | H | 5-Cl | H | |
| 214 | COOC$_2$H$_5$ | H | SO$_2$—CH$_2$COOC$_2$H$_5$ | H | 5-Cl | H | resin |
| 215 | COOC$_2$H$_5$ | H | S—CH$_2$CH$_2$OH | oil | | | |
| 216 | COOC$_2$H$_5$ | H | S—CH$_2$CH$_2$OCH$_3$ | H | 5-Cl | H | (1.5678) |
| 217 | COOC$_2$H$_5$ | H | SO—CH$_2$CH$_2$OCH$_3$ | H | 5-Cl | H | |
| 218 | COOC$_2$H$_5$ | H | SO$_2$—CH$_2$CH$_2$OCH$_3$ | H | 5-Cl | H | resin |
| 219 | COOC$_2$H$_5$ | H | S—CH$_2$CH$_2$N(C$_2$H$_5$)$_2$ | H | 5-Cl | H | 96–98 |
| 220 | COOC$_2$H$_5$ | H | S—CH$_2$CH$_2$CONHPh | H | 5-Cl | H | oil |
| 221 | COOC$_2$H$_5$ | H | S—(CH$_2$)$_3$—SH | H | 5-Cl | H | |
| 222 | COOC$_2$H$_5$ | H | (see structure below) | H | 5-Cl | H | 110–112 |

Example 222 structure: 5-chloroquinolin-8-yloxy linked to CH$_2$-CH(SCH$_2$CH$_2$S—)-CH$_2$-C(=O)-O-ethyl

C. Biological Examples

EXAMPLE 1

Wheat and barley are grown in the greenhouse in plastic pots until they have reached the 3- to 4-leaf stage and then treated in succession with the compounds according to the invention and the herbicides by the post-emergence method. The herbicides and the compounds of the formula I are applied in the form of aqueous suspensions or emulsions at a water application rate of 300 l/ha (converted). 3–4 Weeks after the treatment, the plants are scored visually for any type of damage caused by the herbicides which have been applied, and, in particular, the extent of sustained growth inhibition is taken into account. The assessment is given in percentages compared with the untreated controls.

Even when unduly high dosages of the herbicide were used, severe damage in the crop plants is markedly reduced and lesser damage prevented completely.

The mixtures of herbicides and compounds according to the invention are therefore outstandingly suitable for the selective control of weeds in cereal crops.

EXAMPLE 2

Maize plants are grown in the greenhouse in plastic pots until they have reached the 4- to 5-leaf stage and treated by the post-emergence method using herbicides together with compounds of the formula I according to the invention. The active substances are applied in the form of aqueous suspensions or emulsions at a water application rate of 300 l/ha (converted). 4 weeks after the treatment, the plants are scored visually for any type of damage caused by the herbicides which have been applied, and, in particular, the extent of sustained growth inhibition is taken into account.

The assessment is given in percentages compared with the untreated controls.

Table 2 compiles a few test results.

The results show that the compounds of the formula I according to the invention which have been used are capable of effectively reducing severe herbicide damage to the maize plants. Even when unduly high dosages of the herbicide were used, severe damage in the crop plants is markedly reduced and lesser damage prevented completely. The mixtures of herbicides and compounds of the formula are therefore outstandingly suitable for the selective control of weeds in maize.

TABLE 2

Effectiveness of the compounds according to the invention

| Active substance(s) | g of a.i./ha dosage rate | Damage in % Maize |
|---|---|---|
| Herbicide H | 200 | 70 |
|  | 100 | 65 |
|  | 50 | 50 |
|  | 25 | 40 |
| H + Example 144 | 200 + 100 | 30 |
|  | 100 + 50 | 20 |
|  | 50 + 25 | 10 |
|  | 25 + 12.5 | 0 |
| H + Example 212 | 200 + 100 | 50 |
|  | 100 + 50 | 40 |
|  | 50 + 25 | 20 |
|  | 25 + 12.5 | 5 |
| H + Example 171 | 200 + 100 | 40 |
|  | 100 + 50 | 30 |
| H + Example 110 | 200 + 100 | 25 |
|  | 100 + 50 | 15 |
|  | 50 + 25 | 0 |
|  | 25 + 12.5 | 0 |
| H + Example 181 | 200 + 100 | 30 |
|  | 100 + 50 | 20 |
|  | 50 + 25 | 5 |
|  | 25 + 12.5 | 0 |
| H + Example 113 | 200 + 100 | 40 |
|  | 100 + 50 | 25 |
|  | 50 + 25 | 5 |
|  | 25 + 12.5 | 0 |

Abbreviations:
H = 3-(4,6-dimethoxypyrimidin-2-yl)-1-[3-(N-methylsulfonyl-N-methylamino)pyridin-2-ylsulfonyl]urea
Example(...) = safener of Table 1, Example No. (...)
a.i. = active ingredient (based on pure active substance)

Note: Table 2 row "Herbicide H" includes dosage 50 + 25 20 / 25 + 12.5 10 (as shown on the continued page at top).

EXAMPLE 3

Rice is sown in plastic pots and grown in the greenhouse under ideal growth conditions. When the plants have reached the 4-leaf stage, they are treated with the herbicides and the compounds of the formula I. 3 weeks after the treatment, the plants are scored for any type of herbicide damage, and, in particular, the extent of sustained growth inhibition and thinning is observed. The score figures show that the safeners effectively reduce herbicide damage to rice.

Mixtures of herbicides and the safeneners according to the invention are therefore suitable for selective weed control in rice. The herbicidal activity of the herbicides used against harmful plants is not affected by adding the safeners according to the invention; at the application rates used, it corresponds to the comparison values as they are achieved when only the herbicides are applied.

We claim:

1. A crop plant-protecting composition containing compounds of the formula I or salts thereof

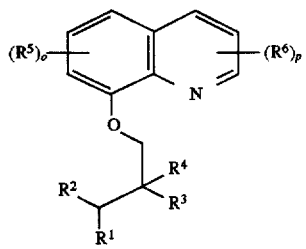

(I)

in which

R¹ radicals have the formula

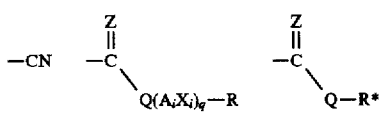

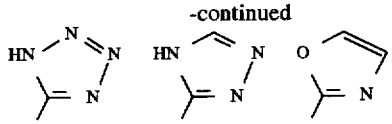

in which R*, R, Z, Q, A$_i$, X$_i$ and q are as defined further below,

R$^2$ is hydrogen, C$_1$–C$_8$-alkyl, C$_1$–C$_8$-haloalkyl, C$_2$–C$_8$-alkenyl, C$_2$–C$_8$-alkynyl, C$_3$–C$_7$-cycloalkyl, benzyl, where each of the last-mentioned six radicals is unsubstituted or substituted by one or more radicals selected from the group consisting of halogen, cyano, nitro, hydroxyl, thio, C$_1$–C$_4$-alkyl, C$_1$–C$_4$-haloalkyl, the latter two substituents only in the case of cyclic radicals, or C$_1$–C$_4$-alkoxy and C$_1$–C$_4$-haloalkoxy, or is SiR$^a{}_3$, in which the R$^a$ radicals independently of one another are C$_1$–C$_4$-alkyl, C$_2$–C$_4$-alkenyl, C$_2$–C$_4$-alkynyl, benzyl, phenyl or substituted phenyl, R$^3$ is OR$^7$, SR$^7$, NR$^8{}_2$, P(Y)R$^9{}_2$, S(O)$_n$—R$^{10}$ or OR$^{10}$, in which n is 0, 1 or 2 and
Y is O or S and
R$^7$, R$^8$, R$^9$ and R$^{10}$ are as defined further below, R$^4$ is hydrogen, C$_1$–C8-alkyl, C$_1$–C$_8$-haloalkyl, C$_2$–C$_8$-alkenyl, C$_2$–C$_8$-alkynyl, C$_3$–C$_7$-cycloalkyl, benzyl, where each of the last-mentioned six radicals is unsubstituted or substituted by one or more radicals selected from the group consisting of halogen, cyano, nitro, hydroxyl, thio, C$_1$–C$_4$-alkyl, C$_1$–C$_4$-haloalkyl, the latter two substituents only in the case of cyclic radicals, or C$_1$–C$_4$-alkoxy and C$_1$–C$_4$-haloalkoxy, or is OR$^{11}$ or S(O)$_n$—R$^{11}$, or R$^3$ and R$^4$ together are =O, =S or a diradical of the formula —Q$^1$—A—Q$^2$—, in which Q$^1$ and Q$^2$ are selected from the radicals as defined for Q and A is C$_2$–C$_4$-alkylene or C$_2$–C$_4$-alkenylene, and R$^5$ and R$^6$ are identical or different radicals which, independently of one another, are hydrogen, halogen, nitro, cyano, amino or C$_1$–C$_8$-alkyl, C$_1$–C$_4$-acyl, C$_1$–C$_8$-alkoxy, mono(C$_1$–C$_4$-alkyl)amino, di(C$_1$–C$_4$-alkyl)amino, C$_1$–C$_8$-alkylthio, C$_1$–C$_8$-alkylsulfinyl or C$_1$–C$_8$-alkylsulfonyl, where each of the last-mentioned eight radicals is unsubstituted or substituted by one or more substituents selected from the group consisting of halogen, nitro, cyano, hydroxyl, thio, C$_1$–C$_8$-haloalkoxy, C–C$_8$-alkoxy, C$_1$–C$_8$-(alkoxypolyalkyleneoxy), C$_1$–C$_8$-alkylthio, C$_1$–C$_6$-alkylsulfinyl, C$_1$–C$_6$-alkylsulfonyl, C$_2$–C$_8$-alkenyloxy, C$_2$–C$_8$-alkynyloxy, C$_2$–C$_8$-alkenylthio, C$_2$–C$_8$-alkynylthio, C$_3$–C$_7$-cycloalkyl, C$_3$–C$_7$-cycloalkoxy, mono and di(C$_1$–C$_4$-alkyl)amino and C$_1$–C$_8$-alkoxycarbonyl, o is an integer from 1 to 3,
p is an integer from 1 to 3,
R is hydrogen or an aliphatic, aromatic, heteroaromatic, araliphatic or heteroaliphatic radical having 1 to 30 carbon atoms and, if appropriate, one or more functional groups, R* is a radical of the formula —CO—R, —CS—R, —NR$^h$R$^i$, —N=CR$^j$R$^k$ or SiR$^m{}_3$, in which R has the abovementioned meaning and R$^h$, R$^i$, R$^j$ and R$^k$ independently of one another are hydrogen, C$_1$–C$_4$-alkyl, C$_2$–C$_4$-alkenyl, C$_2$–C$_4$-alkynyl, benzyl, phenyl or substituted phenyl, or R$^h$ and R$^i$ together with the nitrogen atom are a 5- or 6-membered heterocycle which can also contain up to two further heteroatoms selected from the group consisting of N, O and S and which can be substituted by C$_1$–C$_4$-alkyl, or R$^i$ and R$^k$ together are a C$_2$–C$_6$-alkylene group and the radicals R$^m$, independently of one another, are C$_1$–C$_4$-alkyl, C$_2$–C$_4$-alkenyl, C$_2$–C$_4$-alkynyl, benzyl, phenyl or substituted phenyl, R$^7$ is a radical selected from the radicals as defined for R*, R$^8$ radicals independently of one another are hydrogen, C$_1$–C$_4$-alkyl, C$_1$–C$_4$-haloalkyl, C$_2$–C$_4$-alkenyl, C$_2$–C$_4$-alkynyl, C$_3$–C$_6$-cycloalkyl, C$_3$–C$_6$-cycloalkenyl, heterocyclyl, aryl or heteroaryl, R$^9$ radicals independently of one another are hydrogen, C$_1$–C$_8$-alkyl, C$_1$–C$_8$-haloalkyl, C$_2$–C$_8$-alkenyl, C$_2$–C$_8$-alkynyl, C$_3$–C$_7$-cycloalkyl, C$_1$–C$_8$-alkoxy, C$_2$–C$_8$-alkenyloxy, C$_2$–C$_8$-alkynyloxy, C$_1$–C$_8$-haloalkoxy, C$_3$–C$_7$-cycloalkoxy, phenyl, phenoxy, the last-mentioned two radicals in the phenyl ring being unsubstituted or substituted by one or more radicals selected from the group consisting of halogen, cyano, C$_1$–C$_4$-alkyl, C$_1$–C$_4$-alkoxy, C$_1$–C$_4$-haloalkyl, C$_1$–C$_4$-haloalkoxy and nitro, R$^{10}$ is a radical which is selected from the radicals as defined for R, R$^{11}$ is a radical which is selected from the radicals as defined for R, Z is O, S, NR$^8$, NOR$^8$ or N—O—CO—R$^{12}$, R$^{12}$ is C$_1$–C$_4$-alkyl, C$_1$–C$_4$-haloalkyl, C$_2$–C$_4$-alkenyl, C$_2$–C$_4$-alkynyl, C$_3$–C$_6$-cycloalkyl, C$_3$–C$_6$-cycloalkenyl, heterocyclyl, aryl or heteroaryl, Q is O, S, NR$^8$ or NR$^8$—NR$^8$, X$_i$ radicals independently of one another are O, S, NR$^8$ or N—(A$_i$X$_i$)$_q$—R, A$_i$ radicals independently of one another are C$_1$–C$_6$-alkylene, C$_2$–C$_6$-alkenylene, C$_2$–C$_6$-alkynylene, C$_3$–C$_6$-cycloalkylene, C$_3$–C$_6$-cycloalkenylene, heterocyclylene, arylene or heteroarylene, i is a consecutive number which, if q is unequal to 0, assumes the meaning of all integers from 1 to q, where q has the meaning given below, q indices independently of one another are integers from 0 to 4, the total of the numbers q being limited, and conventional formulation auxiliaries wherein substituted phenyl, unless otherwise defined, is phenyl substituted by one or more radicals from the group consisting of halogen, alkyl, haloalkyl, alkoxy, haloalkoxy, hydroxy, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl, and in case of radicals having carbon atoms, having in each case 1 to 4 carbon atoms.

2. A composition as claimed in claim 1, wherein

R$^2$ is hydrogen, C$_1$–C$_4$-alkyl, C$_1$–C$_4$-haloalkyl, C$_5$–C$_6$-cycloalkyl, benzyl, trimethylsilyl or triethylsilyl R$^3$ is OR$^7$, NR$^8{}_2$, S(O)$_n$—R$^{10}$ or OR$^{10}$, in which
n is 0, 1 or 2, and
R$^7$, R$^8$ and R$^{10}$ have the abovementioned meanings, or in which, R$^4$ is hydrogen, C$_1$–C$_4$-alkyl, C$_1$–C$_4$-haloalkyl, C$_2$–C$_4$-alkenyl, C$_2$–C$_4$-alkynyl, C$_5$–C$_6$-cycloalkyl, benzyl or OR$^{11}$, in which R$^{11}$ has the abovementioned meaning, or R$^3$ and R$^4$ together are =O or a diradical of the formula
—SCH$_2$CH$_2$CH$_2$S—, —SCH$_2$CH$_2$S—, —OCH$_2$CH$_2$CH$_2$—O— or —OCH$_2$CH$_2$O—, $R^5$ and $R^6$ are identical or different radicals which, independently of one another, are hydrogen, halogen, nitro, cyano, amino or $C_1$–$C_4$-haloalkyl, $C_1$–$C_4$-haloalkoxy, $C_1$–$C_4$-alkyl, $C_1$–$C_4$-alkoxy, mono($C_1$–$C_4$-alkyl)amino, di($C_1$–$C_4$-alkyl)amino, $C_1$–$C_4$-alkylthio, $C_1$–$C_4$-alkylsulfonyl.

3. A composition as claimed in claim 1, wherein

R is hydrogen, $C_1$–$C_{18}$-alkyl, $C_3$–$C_{12}$-cycloalkyl, $C_2$–$C_8$-alkenyl, $C_2$–$C_8$-alkynyl, heterocyclyl, phenyl or heteroaryl, where each of the above radicals independently of one another is unsubstituted or substituted by one or more radicals selected from the group consisting of halogen, cyano, nitro, thio, hydroxyl, $C_1$–$C_8$-alkyl, $C_1$–$C_8$-haloalkyl, the latter two substituents only in the case of cyclic radicals, or $C_1$–$C_8$-alkoxy, $C_2$–$C_8$-alkenyloxy, $C_2$–$C_8$-alkynyloxy, $C_1$–$C_8$-haloalkoxy, $C_1$–$C_8$-alkylthio, $C_2$–$C_8$-alkenylthio, $C_2$–$C_8$-alkynylthio, $C_3$–$C_7$-cycloalkyl, $C_3$–$C_7$-cycloalkoxy, radicals of the formulae —$NR^bR^c$, —CO—$NR^bR^c$ and —O—CO—$NR^bR^c$, where $R^b$ and $R^c$ in the last-mentioned three radicals independently of one another are hydrogen, $C_1$–$C_8$-alkyl, $C_2$–$C_8$-alkenyl, $C_2$–$C_8$-alkynyl, benzyl, phenyl or substituted phenyl or, together with the nitrogen atom, are a 3- to 8-membered heterocycle which can also contain up to two further heteroatoms selected from the group consisting of N, O and S and which can be substituted by $C_1$–$C_4$-alkyl, and also ($C_1$–$C_8$-alkoxy)carbonyl, ($C_1$–$C_8$-alkoxy)thiocarbonyl, ($C_2$–$C_8$-alkenyloxy)carbonyl, ($C_2$–$C_8$-alkynyloxy)carbonyl, ($C_1$–$C_8$-alkylthio)carbonyl, ($C_2$–$C_8$-alkenylthio)carbonyl, ($C_2$–$C_8$-alkynylthio)carbonyl, formyl, ($C_1$–$C_8$-alkyl)carbonyl, ($C_2$–$C_8$-alkenyl)carbonyl, ($C_2$–$C_8$-alkynyl) carbonyl, $C_1$–$C_4$-alkylimino, $C_1$–$C_4$-alkoximino, ($C_1$–$C_8$-alkyl) carbonylamino, ($C_2$–$C_8$-alkenyl)carbonylamino, ($C_2$–$C_8$-alkynyl)carbonylamino, ($C_1$–$C_8$-alkoxy)carbonylamino, ($C_2$–$C_8$-alkenyloxy)carbonylamino, ($C_2$–$C_8$-alkynyloxy)carbonylamino, ($C_1$–$C_8$-alkylamino)carbonylamino, ($C_1$–$C_8$-alkyl) carbonyloxy, which is unsubstituted or substituted by halogen, nitro, $C_1$–$C_4$-alkoxy or optionally substituted phenyl, and also ($C_2$–$C_6$-alkenyl)carbonyloxy, ($C_2$–$C_6$-alkynyl)carbonyloxy, ($C_1$–$C_8$-alkyloxy)carbonyloxy, ($C_2$–$C_6$-alkenyloxy)carbonyloxy, ($C_2$–$C_6$-alkynyloxy)carbonyloxy, $C_1$–$C_8$-alkylsulfonyl, $C_1$–$C_8$-alkylsulfinyl, phenyl, phenyl-$C_1$–$C_6$-alkoxy, phenyl ($C_1$–$C_6$-alkoxy)carbonyl, phenoxy, phenoxy-$C_1$–$C_6$-alkoxy, phenoxy($C_1$–$C_6$-alkoxy)carbonyl, phenoxycarbonyl, phenylcarbonyloxy, phenylcarbonylamino, phenyl ($C_1$–$C_6$-alkyl) carbonylamino and phenyl($C_1$–$C_6$-alkyl)carbonyloxy, the last-mentioned eleven radicals being unsubstituted in the phenyl ring or substituted by one or more radicals selected from the group consisting of halogen, cyano, $C_1$–$C_4$-alkyl, $C_1$–$C_4$-alkoxy, $C_1$–$C_4$-haloalkyl, $C_1$–$C_4$-haloalkoxy and nitro, and also radicals of the formulae —$SiR^d_3$, —O—$Si(R^d)_3$ and $(R^d)_3Si$—$C_1$–$C_6$-alkoxy, where the $R^d$ radicals in the abovementioned formulae, independently of one another, are $C_1$–$C_4$-alkyl, $C_2$–$C_4$-alkenyl, $C_2$–$C_4$-alkynyl, benzyl, phenyl or substituted phenyl, and —CO—$ONR^e_2$, —O—N=$CR^e_2$, —N=$CR^e_2$, —O—$NR^e_2$, —$CH(OR^e)_2$ and —O—$(CH_2)_m$—$CH(OR^e)_2$, where the $R^e$ radicals in the abovementioned formulae, independently of one another, are hydrogen, $C_1$–$C_4$-alkyl or phenyl which is unsubstituted or mono- or polysubstituted by radicals selected from the group consisting of halogen, cyano, $C_1$–$C_4$-alkyl, $C_1$–$C_4$-alkoxy, $C_1$–$C_4$-haloalkyl, $C_1$–$C_4$-haloalkoxy and nitro, or, in pairs, is a $C_2$–$C_6$-alkylene chain and m is 0 to 6, and a substituted radical of the formula $R^fO$—$CHR^g$—$CH(OR^f)$—, in which the $R^f$ radicals, independently of one another, are $C_1$–$C_4$-alkyl or together are a $C_1$–$C_6$-alkylene group and $R^g$ is hydrogen or $C_1$–$C_4$-alkyl, and a radical of the formula I'

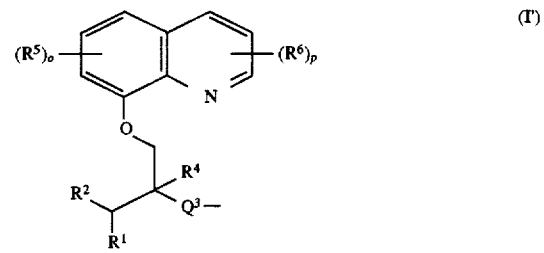

in which $R^1$, $R^2$, $R^4$, $R^5$, $R^6$, o and p are defined in formula I and $Q^3$ is selected from the radicals as defined for Q.

4. A composition as claimed in claim 1, wherein

R is hydrogen, $C_1$–$C_8$-alkyl, $C_4$–$C_7$-cycloalkyl, $C_2$–$C_8$-alkenyl or $C_2$–$C_8$-alkynyl, heterocyclyl, phenyl or heteroaryl, where each of the last-mentioned seven radicals, independently of one another, is unsubstituted or substituted by one or more radicals selected from the group consisting of halogen, cyano, nitro, thio, hydroxyl, $C_1$–$C_4$-alkyl, $C_1$–$C_4$-haloalkyl, the latter two substituents only in the case of cyclic radicals, $C_1$–$C_4$-alkoxy, $C_2$–$C_4$-alkenyloxy, $C_2$–$C_4$-alkynyloxy, $C_1$–$C_4$-haloalkoxy, $C_1$–$C_4$-alkylthio, $C_2$–$C_4$-alkenylthio, $C_2$–$C_4$alkynylthio, $C_5$–$C_6$-cycloalkyl, $C_5$–$C_6$-cycloalkoxy, amino, mono- and di($C_1$–$C_4$-alkyl)amino, ($C_1$–$C_6$-alkoxy)carbonyl, radicals of the formula —$SiR^d_3$, in which the $R^d$ radicals independently of one another are $C_1$–$C_4$-alkyl, benzyl or phenyl, and radicals of the formulae —O—$NR^e_2$, —O—N=$CR^e_2$, —N=$CR^e_2$, —$CH(OR^e)_2$, in which the $R^e$ radicals in the abovementioned formulae, independently of one another, are hydrogen, $C_1$–$C_4$-alkyl or phenyl, or, in pairs, are a $C_2$–$C_5$-alkylene chain, $R^*$ and $R^7$, independently of one another, are a radical of the formula —CO—R, —$NR^hR^i$ or —N=$CR^jR^k$, $R^{10}$ and $R^{11}$, independently of one another, are hydrogen, $C_1$–$C_8$-alkyl, $C_5$–$C_6$-cycloalkyl, $C_2$–$C_8$-alkenyl or $C_2$–$C_8$-alkynyl, where each of the last-mentioned four radicals, independently of one another, is unsubstituted or substituted by one or more radicals selected from the group consisting of halogen, cyano, nitro, $C_1$–$C_4$-alkoxy, $C_2$–$C_4$-alkenyloxy, $C_2$–$C_4$-alkynyloxy, $C_5$–$C_6$-cycloalkyl, $C_5$–$C_6$-cycloalkoxy, mono- and di($C_1$–$C_4$-alkyl)amino, radicals of the formula —$SiR^d_3$, in which the $R^d$ radicals, independently of one another, are $C_1$–$C_2$-alkyl or phenyl, and radicals of the formulae —O—N=$CR^e_2$ and —N=$CR^e_2$, in which the $R^e$ radicals in the abovementioned formulae, independently of one another, are hydrogen, $C_1$–$C_2$-alkyl or phenyl, or, in pairs, are a $C_2$–$C_5$-alkylene chain, and $R^h$ and $R^i$, independently of one another, are hydrogen, $C_1$–$C_2$-alkyl, benzyl or phenyl or, together with the nitrogen atom, are pyrrolidin-1-yl, piperidin-1-yl, morpholin-4-yl, piperazin-1-yl or imidazol-1-yl, or $R^j$ and $R^k$, independently of one another, are hydrogen, $C_1$–$C_2$-alkyl, benzyl or phenyl or, together, are a $C_4$–$C_5$-alkylene chain.

5. A composition as claimed in claim 1, wherein the herbicide which it contains is from the group of the carbamates, thiocarbamates, haloacetanilides, substituted phenoxy-, naphthoxy- and phenoxyphenoxycarboxylic acid derivatives and heteroaryloxyphenoxyalkanecarboxylic acid derivatives, cyclohexanedione derivatives, imidazolinones, pyrimidyloxypyridinecarboxylic acid derivatives, pyrimidyloxybenzoic acid derivatives, sulfonylureas and triazolopyrimidinesulfonamide derivatives.

6. A compound of formula (I) or a salt thereof

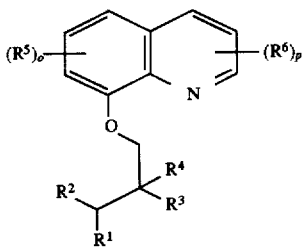
(I)

wherein

R$^1$ is a radical of the formula —CO—O—R, in which R is as defined below,

R$^2$ is hydrogen,

R$^3$ is S(O)$_n$—R$^{10}$ or OR$^{10}$, where n is 0, 1 or 2 and is R$^{10}$ as defined below, R$^4$ is hydrogen, the radicals R$^5$, same or different, are hydrogen, halogen, nitro, cyano, C$_1$–C$_8$-alkyl, C$_1$–C$_8$-alkoxy or CF$_3$, R$^6$ is hydrogen, o is 1, 2 or 3 p is 1, 2 or 3

R is hydrogen, C$_1$–C$_8$-alkyl, which is unsubstituted or substituted by one or more radicals from the group consisting of halogen, cyano, nitro, C$_1$–C$_4$-alkoxy, C$_2$–C$_8$-alkenyl or C$_2$–C$_8$-alkinyl, and R$^{10}$ is hydrogen, C$_1$–C$_8$-alkyl, which is unsubstituted or substituted by one or more radicals selected from the group consisting of halogen, hydroxy, thiol, cyano, nitro, C$_1$–C$_4$-alkoxy, C$_2$–C$_4$-alkenyloxy, C$_2$–C$_4$-alkinyloxy, mono- and di-(C$_1$–C$_4$-alkyl)-amino and (C$_1$–C$_6$-alkoxy)-carbonyl, or is C$_5$–C$_6$-cycloalkyl, C$_2$–C$_8$-alkenyl, C$_2$–C$_8$-alkinyl, benzyl, phenyl, wherein phenyl unsubstituted or substituted by one or more radicals selected from the group consisting of halogen, C$_1$–C$_4$-alkyl, C$_1$–C$_4$-alkoxy, C$_1$–C$_4$-haloalkyl, C$_1$–C$_4$-haloalkoxy and nitro.

7. A compound as claimed in claim 6, wherein R$^3$ is S—R$^{10}$.

8. A compound as claimed in claim 6, wherein the radicals R$^5$ are same or different and are H, halogen, nitro, cyano, C$_1$–C$_4$-alkyl or C$_1$–C$_4$-alkoxy, R is H or C$_1$–C$_8$-alkyl and R$^{10}$ is H, C$_1$–C$_8$-alkyl or (C$_1$–C$_4$-alkoxy)-carbonylmethyl.

9. A process for the preparation of compounds of the formula I or salts thereof as claimed in claim 6, wherein a) in the event that R$^3$ in formula I is NR$^6{}_2$, OR$^{10}$ or SR$^{10}$, a compound of the formula II

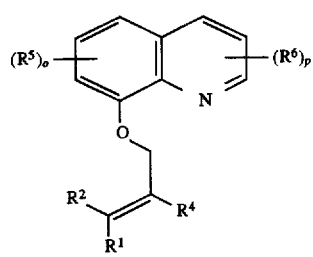
(II)

is reacted with a compound of the formula H—NR$^8$ or H—OR$^{10}$, if appropriate in the presence of a base, R$^8$ and R$^{10}$ being defined as in the abovementioned formula (I), or, b) in the event that R$^3$ in formula I is P(O)R$^9{}_2$, a compound of the formula II

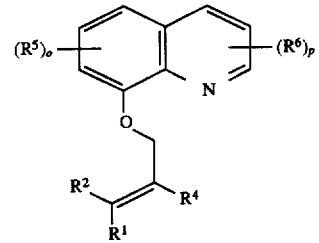
(II)

is reacted with a compound of the formula P(OR)R$^9{}_2$, or with a compound of the formula PH(O)R$^9{}_2$ in the presence of a base, R$^9$ being as defined in formula I and R being selected from the radicals as defined in formula I, or, c) in the event that R$^3$ in formula I is NR$^{82}$, OR$^{10}$ or SR$^{10}$, a compound of the formula III

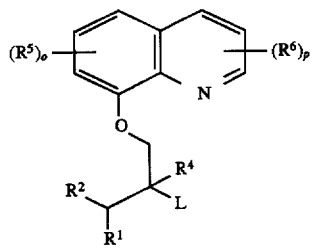
(III)

is reacted with a compound of the formula H—NR$^{82}$, H—OR$^{10}$ or H—SR$^{10}$, if appropriate in the presence of a base, where L is a leaving group and R$^8$ and R$^{10}$ are defined as in the abovementioned formula I, or, d) in the event that R$^3$ in formula 1 is hydroxyl, a compound of the formula IV

(IV)

is reacted with a compound of the formula V

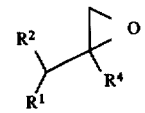
(V)

in the presence of a base, or e) in the event that R$^3$ in formula I is hydroxyl, a compound of the formula VI

is reacted with a compound of the formula VII

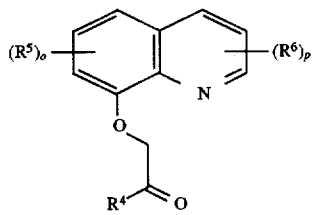

in which M is a metal or metal halide, or, f) in the event that $R^3$ in formula I is $S(O)_n$—$R^{10}$ and n is 1 or 2, a compound of the formula VIII

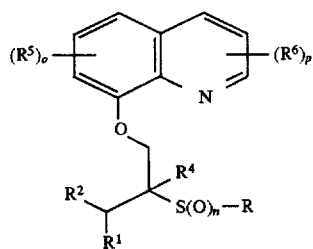

in which n is 0 or 1 and $R^{10}$ is defined as in the abovementioned formula I, is oxidized with an oxidant to give a compound VIII', which corresponds to the abovementioned compound VIII, but n is now greater and, as in formula I, is 1 or 2, or, g) in the event that $R^3$ and $R^4$ in formula I together are =O, a compound of the formula IX

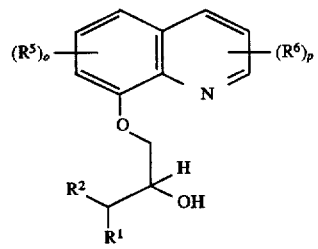

is oxidized with an oxidant to give the compound of the formula X

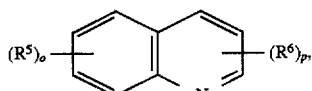

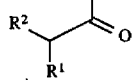

or, h) in the event that $R^3$ and $R^4$ in formula I together are a diradical of the formula —$Q^1$—A—$Q^2$—, in which A, $Q^1$ and $Q^2$ are defined as in formula I, a compound of the abovementioned formula (X) is reacted with a compound of the formula H—$Q^1$—A—$Q^2$—H, the symbols $R^1$, $R^2$, $R^3$, $R^4$, $R^5$, $R^6$, o and p in the above-mentioned formulae II, III, IV, V, VI, VII, VIII, IX and X of variants a) to h) being defined as in formula I.

10. A method of protecting crop plants against phytotoxic side-effects of herbicides, which comprises applying an effective amount of at least one compound of the formula I or a salt thereof as claimed in claim 1 before, after or simultaneously with the abovementioned herbicidal active substance to the plants, the seeds of the plants or the area under cultivation.

11. The method as claimed in claim 10, wherein the crop plants are cereal plants, rice plants or maize plants.

12. The method as claimed in claim 10, wherein the compounds of the formula I or a salt thereof are applied at an application rate of 0.001 to 5 kg/ha of active ingredient and a ratio by weight of safener:herbicide of 1:10 to 10:1.

* * * * *